United States Patent
Shalev et al.

(10) Patent No.: US 10,039,245 B2
(45) Date of Patent: Aug. 7, 2018

(54) HIGH YIELD TOMATO PLANTS

(71) Applicant: VILMORIN & CIE, Paris (FR)

(72) Inventors: Gil Shalev, Ramot Meir (IL); Varda Ashkenazi, Yavne (IL)

(73) Assignee: VILMORIN & CIE, Paris (FR)

(*) Notice: Subject to any disclaimer, the term of this patent is extended or adjusted under 35 U.S.C. 154(b) by 0 days.

(21) Appl. No.: 14/394,599

(22) PCT Filed: Apr. 18, 2013

(86) PCT No.: PCT/IB2013/053076
§ 371 (c)(1),
(2) Date: Oct. 15, 2014

(87) PCT Pub. No.: WO2013/156958
PCT Pub. Date: Oct. 24, 2013

(65) Prior Publication Data
US 2015/0096076 A1    Apr. 2, 2015

Related U.S. Application Data

(60) Provisional application No. 61/635,347, filed on Apr. 19, 2012.

(51) Int. Cl.
| | | |
|---|---|---|
| *A01H 5/08* | (2018.01) | |
| *A01H 5/00* | (2018.01) | |
| *A01H 1/00* | (2006.01) | |
| *A01H 1/04* | (2006.01) | |
| *C12N 5/04* | (2006.01) | |
| *C12Q 1/6895* | (2018.01) | |
| *C12N 15/00* | (2006.01) | |

(52) U.S. Cl.
CPC ............ *A01H 5/08* (2013.01); *A01H 1/04* (2013.01); *A01H 5/00* (2013.01); *C12N 5/04* (2013.01); *C12Q 1/6895* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 5,817,913 A | 10/1998 | Schaffer | |
| 2011/0023176 A1* | 1/2011 | Bunn | A01H 5/08 800/268 |
| 2016/0000029 A1* | 1/2016 | Barten | A01H 5/08 800/260 |

FOREIGN PATENT DOCUMENTS

| | | |
|---|---|---|
| WO | 0149105 A1 | 7/2001 |
| WO | 2011026116 A1 | 3/2011 |

OTHER PUBLICATIONS

Larkin et al., Theor. Appl. Genet., vol. 60, 1981, pp. 197-214.*
Lippman et al., The Making of a Compound Inflorescence in Tomato and Related Nightshades, The Plant Cell Online, Jan. 1, 2008, p. 2033, vol. 20—Issue 11, XP55075467, ISSN: 1040-4651, Public Library of Science.
Thouet et al., Repression of Floral Meristem Fate is Crucial in Shaping Tomato Inflorescence, Journal Article, Feb. 2, 2012, vol. 7—Issue 2, Public Library of Science.
Eshed Y et al., A Genome-Wide Search for Wild-Species Alleles that Increase Horticultural Yield of Processing Tomatoes, Theoretical and Applied Genetics, Jan. 1, 1996, pp. 877-886, vol. 9—Issue 5-6, Springer-Verlag, Berlin, Germany.
International Search Report and Written Opinion issued by the European Patent Office dated Aug. 30, 2013 in corresponding International Application No. PCT/IB2013/053076.
International Union for the Protection of New Varieties of Plants, Guidelines for the Conduct of Tests for Distinctiveness, Uniformity, and Stability, XP55075948, Jan. 2001, Retrieved from the Internet: URL:http://www.upov.int/en/publications/tg-rom/tg044/tg_44_10.pdf Geneva, Switzerland.

* cited by examiner

*Primary Examiner* — Phuong Bui

(57) ABSTRACT

The present invention discloses a tomato plant exhibiting a branching inflorescence phenotype. The aforementioned plant produces statistically significant high yield of mature fruits having the characteristics of average individual fruit weight or average individual fruit brix levels or a combination thereof, similar to fruits produced by a tomato line that is used as the normally branched parent line of said tomato plant. It is also within the scope of the present invention to disclose methods for producing the aforementioned tomato plants and uses thereof.

16 Claims, 6 Drawing Sheets

HIGH YIELD TOMATO PLANTS

FIELD OF THE INVENTION

The present invention relates to tomato plants having improved yield characteristics. More particularly, the present invention relates to tomato plants producing high yield of mature fruits, to methods of producing said plants and to the use thereof.

BACKGROUND OF THE INVENTION

Currently practiced approaches for producing plants having agronomically important traits generally rely on conventional plant breeding programs in which plants of a different genotype are generally crossed in order to produce a hybrid with a recognizable agronomically important trait. Such an agronomically important trait may be an easily recognizable morphological characteristic such as fruit size or color, or alternatively traits, which are difficult to evaluate that, may be selected by using indirect selection criteria. One indirect selection criterion for example might be an easily recognized morphological characteristic of the plant which is either genetically linked to the desired trait or a component of the desired trait or contributes to the desired trait.

Many different approaches can be taken to disclose, reveal or have such expressed morphological characteristics in tomato. One of these approaches is the generation of various tomato plant lines in which introgressions of wild tomato were introduced into a cultivated tomato genetic background were generated in efforts to isolate quantitative trait loci or genes underlying the morphological characteristics.

Tomato reproductive development initiates with the termination of the primary shoot meristem into an inflorescence.

Extensive variation in inflorescence complexity is found in the nightshade (Solanaceae) family. In most cultivated tomatoes a sympodial growth system is presented. The sympodial system is composed of superposed branches such that an apparent main axis or stem, comprising successive secondary axes that terminate in a flower, is formed. Such a zigzag branching pattern repeats a few times before terminating, resulting in a cluster of a few flowers. The inflorescences of tomato have been characterized as a cyme or raceme. Cymose inflorescences are mainly determinate. In such a cymose or definite type inflorescence, the growth of the main stem is definite. The main stem produces lateral branches which grow more vigorously than the main axis. As a result of this branching, the plant spreads out above. A cymose branching has several kinds. A uniparous cyme is a cymose type of branching with only one lateral branch produced at a time. It is also known as monochasial or sympodial. It shows two distinct types namely helicoid and scorpioid. A biparous cyme, also known as dichasial, is when two lateral branches develop at a time. In such configuration, the key axis leads to a flower after presenting daughter lateral axis. These kinds of lateral axis as well as other branches also function within the similar way. A multiparous cyme or polychasial is when more than two branches develop at a time. In such inflorescence type, the primary axis leads to a flower after producing numerous lateral branches, which usually forms numerous horizontal flowers and provide an umbel configuration. Racemose inflorescences are indeterminate. Such a racemose or monopodial or indefinite type inflorescence is characterized by a stem that indefinitely grows by the terminal bud. The lateral branches of the main stem are arranged in an acropetal succession (produced successively towards the apex with older branches towards the base and younger ones towards the apex). As a result of this branching the plant appears conical or pyramidal in shape.

According to UPOV guidelines for Tomato *Lycopersicon lycopersicum*, the inflorescence type may be characterized as mainly uniparous or intermediate (partly uniparous and partly multiparous) or mainly multiparous. The inflorescence of determinate growth type varieties may be characterized by the number of inflorescences on main stem, which is estimated as few, medium, or many (UPOV TG/44/10 Guidelines for the conduct of tests for Distinctness, Uniformity and Stability).

A recent study shows a bifurcation of the meristem into a determinate floral and indeterminate inflorescence meristem (Welty et al., 2007).

Wild tomato species with an inflorescence structure that kept iterating to form compound clusters of flowers are long known. This variant form was given the name "compound inflorescence" to distinguish it from the "normal or regular inflorescence" form. Several mutations are known to affect the structure of tomato flower clusters. These mutations include the jointless (j), blind (bl), anantha (an), flsiflora (fa), single flower truss (sft), self pruning (sp), compound inflorescence (s) and iniflura (uf) loci. These mutations were found to affect inflorescence and floral meristem development by blocking the transition, reverting to vegetative growth or controlling the number of flowers per inflorescence (Allen and Sussex 1996; Dielen act al., 1998; Molinero-Rosales et al., 1999, 2004; Schmitz et al 2002; Lifschitz et al., 2006; Quinet et al., 2006; and, Szymkowiak and Irish 2006).

The mutations that control inflorescence development were often found to be pleiotropic, in that they control other aspects of development such as flowering time and formation of an abscission zone on pedicels. For example in all environmental conditions, the sit mutant flowered significantly later than its corresponding Platense (Pl) cultivar. Flowering time of j was consistently delayed compared with Hienz (Hz), and flowering of s mutant was reported to be delayed in winter compared with the Ailsa Craig (AC) cultivar (Quinet et al., 2006). Furthermore, the s mutant was shown to develop highly branched inflorescences bearing up to 300 flowers due to the conversion of floral meristems into inflorescence meristems, resulting in reduced individual fruit weight (Vriesenga and Honma, 1973) Quinet et al., 2006). The studies of Crane and MacArthur noted that simple inflorescence was dominant to compound inflorescence (Crane, 1915; MacArthur, 1928).

The study of Lippman and colleagues, 2008 described the characterization of two genes that affect the structures of tomato flower cluster. The S gene was found to encode transcription factor related to a gene called WUSCHEL HOMEOBOX 9 that is involved in patterning the embryo within the plant seed (in *Arabidopsis thaliana*). The AN gene was found to encode an F-box protein ortholog of a gene called UNUSUAL FLORAL ORGANS that controls the identity of floral organs. Mutations in both genes were found to transform the well known tomato "vine" into a highly branched structure with hundreds of flowers (Lippman et al., 2008). Three independently arisen alleles of s (s-classic, s-multiflora and Rose Quartz Multiflora) were shown to be responsible for the diversity in tomato inflorescence architecture. However, their effect on yield properties of cultivated varieties was not disclosed.

Most of the efforts in researching inflorescence development mutations were focused on *Solanum pimpinellifolium*

L., LA1589 wild tomato related species. This red fruited species produces inflorescences with an average of 20 flowers per cluster. As stated by the publication of Lippman and colleagues, 2008, the s mutant was originally mapped on the long arm of chromosome 2. It was positioned in the region overlapping introgression lines IL2-3 and IL2-4 of the tomato introgression line map (Eshed and Zamir, 1995). In Eshed and Zamir study, 50 introgression lines (ILs) originating from a cross between the green-fruited species *Lycopersicon pennellii* and the cultivated tomato cv M82 were identified. Each of the introgression lines was characterized for quantitative traits associated with yield as compared to the parental species (Eshed and Zamir, 1995). It was found that in homozygous state, IL2-3 and IL2-4 lines showed significant reduction in yield and fruit mass values relative to the control (M82). The heterozygous hybrids of IL2-3 and IL2-4, exhibited lower yield values (IL2-3) or non significant increase in the yield value (IL2-4) and lower fruit mass values relative to the control (Eshed and Zamir, 1995).

Thus, in view of this, it would be useful to have a means and method for distinguishing high yield hybrids from low or non significant yield hybrids.

It is furthermore a long felt need to have means and methods of obtaining cultivated tomato lines with elevated fruit yield.

SUMMARY OF THE INVENTION

The present invention relates to the field of tomato plants having improved yield characteristics and more specifically, to tomato plants producing high yield of mature fruits, to methods of producing the plants and to the use thereof.

It is one object of the present invention to disclose a tomato plant exhibiting a branching inflorescence phenotype, wherein the plant produces statistically significant high yield of mature fruits having the characteristics of average individual fruit weight or average individual fruit brix levels or a combination thereof, similar to fruits produced by a tomato line that is used as the normally branched parent line of the tomato plant.

It is yet another object of the present invention to disclose the tomato plant as defined above, wherein the plant produces statistically significant high yield of mature fruits as compared to a tomato line that is used as the normally branched parent line of the tomato plant, the tomato line lacking the branching inflorescence phenotype.

It is yet another object of the present invention to disclose the tomato plant as defined above, wherein the branching inflorescence phenotype is controlled by a genetic determinant which shows a non-recessive inheritance.

It is yet another object of the present invention to disclose the tomato plant as defined above, wherein the genetic determinant is in a heterozygous configuration.

It is yet another object of the present invention to disclose the tomato plant as defined above, wherein the heterozygous configuration of the genetic determinant confers at least one heterotic phenotypic effect with respect to the statistically significant high yield of mature fruits.

It is yet another object of the present invention to disclose the tomato plant as defined above, wherein the genetic determinant shows incomplete dominant inheritance with respect to the branching phenotype.

It is yet another object of the present invention to disclose the tomato plant as defined above, wherein the branching inflorescence phenotype co-segregates with at least one molecular marker selected from the group consisting of a 271 bp deletion marker having a nucleotide sequence corresponding to the nucleotide sequence as set forth in SEQ ID NO:5, a single nucleotide polymorphism at the position corresponding to position 2197 in SEQ ID NO:6, a single nucleotide polymorphism at the position corresponding to position 2,313 in SEQ ID NO:7, a single nucleotide polymorphism at the position corresponding to position 1,589 in SEQ ID NO:7 and a combination of a single nucleotide polymorphism at the position corresponding to position 2,161 in SEQ ID NO:7 and a single nucleotide polymorphism at the position corresponding to position 2,146 in SEQ ID NO:7.

It is yet another object of the present invention to disclose the tomato plant as defined above, wherein the genome of the plant is characterized by the presence of at least one allele comprising the at least one molecular marker and at least one allele lacking the at least one molecular marker.

It is yet another object of the present invention to disclose the tomato plant as defined above, wherein the plant comprises within its genome at least one allele comprising a polynucleotide segment having the polynucleotide sequence corresponding to the nucleotide sequence as set forth in SEQ ID NO:3 and at least one allele comprising a polynucleotide segment having the polynucleotide sequence corresponding to the nucleotide sequence as set forth in SEQ ID NO:4.

It is yet another object of the present invention to disclose the tomato plant as defined above, wherein at least one of the molecular marker is in a heterozygous configuration.

It is yet another object of the present invention to disclose the tomato plant as defined above, wherein the branching inflorescence phenotype is obtainable from a tomato plant selected from a group consisting of *Solanum lycopersicum* HAG1, grown from seeds deposited with NCIMB Aberdeen AB21 9YA, Scotland, UK on Apr. 11, 2012 under accession number NCIMB 41958; *Solanum lycopersicum* 4468, grown from seeds deposited with NCIMB Aberdeen AB21 9YA, Scotland, UK on Apr. 11, 2012 under accession number NCIMB 41957 and from progenies thereof.

It is yet another object of the present invention to disclose the tomato plant as defined above, wherein the branching inflorescence phenotype obtainable from a tomato plant *Solanum lycopersicum* HAG1, grown from seeds deposited with NCIMB Aberdeen AB21 9YA, Scotland, UK on Apr. 11, 2012 under accession number NCIMB 41958, co-segregates with at least one molecular marker selected from a group consisting of: a 271 bp deletion having the nucleotide sequence corresponding to the nucleotide sequence as set forth in SEQ ID NO:5, a single nucleotide polymorphism at the position corresponding to position 2197 in SEQ ID NO:6 and a combination of a single nucleotide polymorphism at the position corresponding to position 2,161 in SEQ ID NO:7 and a single nucleotide polymorphism at the position corresponding to position 2,146 in SEQ ID NO:7.

It is yet another object of the present invention to disclose the tomato plant as defined above, wherein the branching inflorescence phenotype obtainable from *Solanum lycopersicum* 4468, grown from seeds deposited with NCIMB Aberdeen AB21 9YA, Scotland, UK on Apr. 11, 2012 under accession number NCIMB 41957, co-segregates with at least one molecular marker selected from a group consisting of: a single nucleotide polymorphism at the position corresponding to position 2,313 in SEQ ID NO:7 and a single nucleotide polymorphism at the position corresponding to position 1,589 in SEQ ID NO:7.

It is yet another object of the present invention to disclose the tomato plant as defined above, wherein the branching inflorescence phenotype is conferred by a branching inflorescence allele.

It is yet another object of the present invention to disclose the tomato plant as defined above, wherein the plant comprises within its genome a heterozygous configuration of the branching inflorescence allele.

It is yet another object of the present invention to disclose the tomato plant as defined above, wherein the plant produces mature fruits with average individual brix level of at least about 4 units.

It is yet another object of the present invention to disclose the tomato plant as defined above, wherein the plant produces mature fruits with average individual weight of at least about 90 gr.

It is yet another object of the present invention to disclose the tomato plant as defined above, wherein the plant produces mature fruits with average individual weight of between about 90 gr and about 190 gr.

It is yet another object of the present invention to disclose the tomato plant as defined above, wherein the plant produces mature fruits with average individual weight of between about 120 gr to about 190 gr.

It is yet another object of the present invention to disclose the tomato plant as defined above, wherein the plant is characterized by an increase of at least one parameter selected from a group consisting of: fruit weight yield per plant, fruit weight yield per cluster, number of fruits per plant, number of flowers per plant, number of flowers per cluster, fruit brix*yield, earliness and any combination thereof, as compared to a tomato line that is used as the normally branched parent line of the tomato plant.

It is yet another object of the present invention to disclose the tomato plant as defined above, wherein the plant is characterized by a statistically significant increased fruit weight yield per plant of at least about 8% as compared to the yield of a tomato line that is used as the normally branched parent line of the tomato plant.

It is yet another object of the present invention to disclose the tomato plant as defined above, wherein the plant is characterized by a statistically significant increased fruit weight yield per plant of between about 8% to about 20% as compared to the yield of a tomato line that is used as the normally branched parent line of the tomato plant.

It is yet another object of the present invention to disclose the tomato plant as defined above, wherein the plant is characterized by a statistically significant increased fruit weight yield per plant of at least about 18% as compared to the yield of a tomato plant that is used as the normally branched parent line of the tomato plant.

It is yet another object of the present invention to disclose the tomato plant as defined above, wherein the plant is characterized by an increased average fruit weight yield per cluster of at least about 10% as compared to the yield per cluster of a tomato plant that is used as the normally branched parent line of the tomato plant.

It is yet another object of the present invention to disclose the tomato plant as defined above, wherein the plant is characterized by an increased average fruit weight yield per cluster of between about 12% and about 25% as compared to the yield per cluster of a tomato plant that is used as the normally branched parent line of the tomato plant.

It is yet another object of the present invention to disclose the tomato plant as defined above, wherein the plant is characterized by an increased average fruit weight yield per cluster of at least about 24% as compared to the yield per cluster of a tomato plant that is used as the normally branched parent line of the tomato plant.

It is yet another object of the present invention to disclose the tomato plant as defined above, wherein the plant is characterized by an increased average flower number per cluster of at least about 20% as compared to the average flower number per cluster of a tomato line that is used as the normally branched parent line of the tomato plant.

It is yet another object of the present invention to disclose the tomato plant as defined above, wherein the plant is characterized by an increased average flower number per cluster of between about 20% to about 80% as compared to the average flower number per cluster of a tomato line that is used as the normally branched parent line of the tomato plant.

It is yet another object of the present invention to disclose the tomato plant as defined above, wherein the plant is characterized by an increased average flower number per cluster of at least about 60% as compared to the average flower number per cluster of a tomato line that is used as the normally branched parent line of the tomato plant.

It is yet another object of the present invention to disclose the tomato plant as defined above, wherein the plant is characterized by having an average number of at least about 20 fruits per plant.

It is yet another object of the present invention to disclose the tomato plant as defined above, wherein the plant displays enhanced earliness parameters as compared to a tomato line that is used as the normally branched parent line of the tomato plant.

It is yet another object of the present invention to disclose the tomato plant as defined above, wherein the plant is characterized by a decrease of at least about 15% in the average number of days to first ripen fruit as compared to a tomato line that is used as the normally branched parent line of the tomato plant.

It is yet another object of the present invention to disclose the tomato plant as defined above, wherein the plant is characterized by a decrease of between about 20% and about 50% in the average number of days to first ripen fruit as compared to a tomato line that is used as the normally branched parent line of the tomato plant.

It is yet another object of the present invention to disclose the tomato plant as defined above, wherein the plant is characterized by a decrease of between about 22% and about 35% increase in the average number of days to first ripen fruit as compared to a tomato line that is used as the normally branched parent line of the tomato plant.

It is yet another object of the present invention to disclose the tomato plant as defined above, wherein the normally branched parent line is selected from the group consisting of a Beef type, a Loose type and a Cluster type tomato line.

It is a further object of the present invention to disclose a tomato plant exhibiting a branching inflorescence phenotype, wherein the branching inflorescence phenotype co-segregates with a molecular marker combination selected from the group consisting of a single nucleotide polymorphism at the position corresponding to position 2,313 in SEQ ID NO:7 combined with a 271 bp indel marker having a nucleotide sequence corresponding to the nucleotide sequence as set forth in SEQ ID NO:5, a single nucleotide polymorphism at the position corresponding to position 1,589 in SEQ ID NO:7 combined with a 271 bp indel marker having a nucleotide sequence corresponding to the nucleotide sequence as set forth in SEQ ID NO:5 and a combination thereof.

It is yet another object of the present invention to disclose the plant as defined above, wherein the plant is a hybrid.

It is yet another object of the present invention to disclose the pollen of the tomato plant as defined above.

It is yet another object of the present invention to disclose the ovule of the plant as defined above.

It is yet another object of the present invention to disclose a tomato fruit derived from the tomato plant as defined above.

It is yet another object of the present invention to disclose a tomato fruit product derived from the tomato plant as defined above.

It is yet another object of the present invention to disclose a tomato seed derived from a crossing in which at least one of the parents is a tomato plant as defined above.

It is yet another object of the present invention to disclose a tomato seed from which the tomato plants as defined above originate.

It is yet another object of the present invention to disclose plant part of a tomato plant as defined above.

It is yet another object of the present invention to disclose the seed of the tomato plant as defined above, wherein a plant grown from the seed produces a tomato plant exhibiting a branching inflorescence phenotype, wherein the plant produces statistically significant high yield of mature fruits having the characteristics of average individual fruit weight or average individual fruit brix levels or a combination thereof, similar to fruits produced by a tomato line that is used as the normally branched parent line of the tomato plant.

It is yet another object of the present invention to disclose the seed as defined above, wherein the branching inflorescence phenotype is co-segregating with at least one molecular marker selected from the group consisting of: a 271 bp deletion marker having a nucleotide sequence corresponding to the nucleotide sequence as set forth in SEQ ID NO:5, a single nucleotide polymorphism at the position corresponding to position 2197 in SEQ ID NO:6, a single nucleotide polymorphism at the position corresponding to position 2,313 in SEQ ID NO:7, a single nucleotide polymorphism at the position corresponding to position 1,589 in SEQ ID NO:7 and a combination of a single nucleotide polymorphism at the position corresponding to position 2,161 in SEQ ID NO:7 and a single nucleotide polymorphism at the position corresponding to position 2,146 in SEQ ID NO:7.

It is yet another object of the present invention to disclose the seed as defined above, wherein at least one of the molecular marker is in a heterozygous configuration.

It is yet another object of the present invention to disclose the seed as defined above, wherein the branching inflorescence phenotype is obtainable from a tomato plant selected from a group consisting of Solanum lycopersicum HAG1, grown from seeds deposited with NCIMB Aberdeen AB21 9YA, Scotland, UK on Apr. 11, 2012 under accession number NCIMB 41958; Solanum lycopersicum 4468, grown from seeds deposited with NCIMB Aberdeen AB21 9YA, Scotland, UK on Apr. 11, 2012 under accession number NCIMB 41957 and from progenies thereof.

It is yet another object of the present invention to disclose the seed as defined above, wherein the plant is characterized by an increase of at least one parameter selected from a group consisting of fruit weight yield per plant, fruit weight yield per cluster, number of fruits per plant, number of flowers per plant, number of flowers per cluster, fruit brix*yield, earliness and any combination thereof, as compared to a tomato line that is used as the normally branched parent line of the tomato plant.

It is yet another object of the present invention to disclose the tomato plant as defined above, wherein the plant further comprising within its genome at least one additional trait selected from the group consisting of high germination rate, vigorous growth, herbicide resistance, insect resistance, resistance to bacterial, fungal or viral disease, and resistance to a non-biotic stress, wherein the additional trait is introduced by a method selected from the group consisting of breeding, genetic determinant introgression and transformation.

It is yet another object of the present invention to disclose a tissue culture of regenerable cells or protoplasts obtained from the tomato plant as defined above or a part thereof.

It is yet another object of the present invention to disclose the tissue culture as defined above, wherein the regenerable cells or protoplasts are obtainable from a plant part selected from the group consisting of leaves, pollen, embryos, immature embryos, roots, root tips, anthers, meristematic cells, microspores, flowers, cotyledons, pistil, fruit, seeds, seed coat or any combination thereof.

It is yet another object of the present invention to disclose the tissue culture as defined above, wherein the regenerable cells comprise cells or protoplasts or callus.

It is yet another object of the present invention to disclose the tissue culture as defined above, wherein the tissue culture regenerates plants having a branching inflorescence phenotype, wherein the plant produces statistically significant high yield of mature fruits having the characteristics of average individual fruit weight or average individual fruit brix levels or a combination thereof, similar to fruits produced by a tomato line that is used as the normally branched parent line of the tomato plant.

It is yet another object of the present invention to disclose a cell derived from a tissue culture as defined above.

It is yet another object of the present invention to disclose a tomato plant regenerated from the tissue culture as defined above.

It is yet another object of the present invention to disclose a tomato plant exhibiting a branching inflorescence phenotype, wherein the plant produces statistically significant high yield of mature fruits having the characteristics of average individual fruit weight or average individual fruit brix levels or a combination thereof, similar to fruits produced by a tomato line that is used as the normally branched parent line of the tomato plant, further wherein the branching inflorescence phenotype co-segregates with at least one molecular marker selected from a group consisting of: a 271 bp deletion having the nucleotide sequence corresponding to the nucleotide sequence as set forth in SEQ ID NO:5, a single nucleotide polymorphism at the position corresponding to position 2197 in SEQ ID NO:6 and a combination of a single nucleotide polymorphism at the position corresponding to position 2,161 in SEQ ID NO:7 and a single nucleotide polymorphism at the position corresponding to position 2,146 in SEQ ID NO:7.

It is yet another object of the present invention to disclose the tomato plant as defined above, wherein the fruit yield produced by the plant is similar or higher than the fruit yield produced by a tomato plant having a branching inflorescence phenotype co-segregating with at least one molecular marker selected from a group consisting of a single nucleotide polymorphism at the position corresponding to position 2,313 in SEQ ID NO:7 and a single nucleotide polymorphism at the position corresponding to position 1,589 in SEQ ID NO:7.

It is yet another object of the present invention to disclose a tomato plant exhibiting a branching inflorescence phenotype, wherein the plant produces statistically significant high yield of mature fruits having the characteristics of average individual fruit weight or average individual fruit brix levels or a combination thereof, similar to fruits produced by a tomato line that is used as the normally branched parent line of the tomato plant, further wherein the branching inflorescence phenotype co-segregates with at least one molecular marker selected from a group consisting of: a single nucleotide polymorphism at the position corresponding to position 2,313 in SEQ ID NO:7 and a single nucleotide polymorphism at the position corresponding to position 1,589 in SEQ ID NO:7.

It is yet another object of the present invention to disclose the tomato plant as defined above, wherein the fruit yield produced by the plant is similar or higher than the fruit yield produced by a tomato plant having a branching inflorescence phenotype co-segregating with at least one molecular marker selected from a group consisting of: a 271 bp deletion having the nucleotide sequence corresponding to the nucleotide sequence as set forth in SEQ ID NO:5, a single nucleotide polymorphism at the position corresponding to position 2197 in SEQ ID NO:6 and a combination of a single nucleotide polymorphism at the position corresponding to position 2,161 in SEQ ID NO:7 and a single nucleotide polymorphism at the position corresponding to position 2,146 in SEQ ID NO:7.

It is yet another object of the present invention to disclose a tomato field or tomato greenhouse comprising tomatoes as defined above.

It is yet another object of the present invention to disclose a method for producing a tomato plant exhibiting a branching inflorescence phenotype, wherein the plant produces statistically significant high yield of mature fruits having the characteristics of average individual fruit weight or average individual fruit brix levels or a combination thereof, similar to fruits produced by a tomato line that is used as the normally branched parent line of the tomato plant, the method comprising the steps of: (a) selecting a first tomato plant having a highly branching inflorescence phenotype or a branching inflorescence phenotype and a second tomato plant used as a normally branched parent line; (b) crossing the first and the second tomato plants of step (a) to produce an F1 tomato plant progeny; and (c) evaluating fruit yield parameters of the progeny, and selecting at least one plant producing statistically significant high yield of mature fruits having the characteristics of average individual fruit weight or average individual fruit brix levels or a combination thereof, similar to fruits produced by a tomato line that is used as the normally branched parent line of the tomato plant.

It is yet another object of the present invention to disclose the method as defined above, comprising additional steps of: (a) analyzing a DNA sample obtained from the progeny of step (b) for the presence of at least one molecular marker selected from the group consisting of: a 271 bp deletion marker having a nucleotide sequence corresponding to the nucleotide sequence as set forth in SEQ ID NO:5, a single nucleotide polymorphism at the position corresponding to position 2197 in SEQ ID NO:6, a single nucleotide polymorphism at the position corresponding to position 2,313 in SEQ ID NO:7, a single nucleotide polymorphism at the position corresponding to position 1,589 in SEQ ID NO:7 and a combination of a single nucleotide polymorphism at the position corresponding to position 2,161 in SEQ ID NO:7 and a single nucleotide polymorphism at the position corresponding to position 2,146 in SEQ ID NO:7, the at least one molecular marker is co-segregating with the branching inflorescence phenotype; and (b) selecting at least one plant having the characteristics of step (a).

It is yet another object of the present invention to disclose the method as defined above, comprising an additional step of selecting the parameter from a group consisting of: fruit weight yield per plant, fruit weight yield per cluster, number of fruits per plant, number of flowers per plant, number of flowers per cluster, average fruit weight, average fruit brix, fruit brix*yield, earliness and any combination thereof.

It is yet another object of the present invention to disclose the method as defined above, comprising an additional step of selfing the F1 tomato plants of step (b) to produce F2 tomato plant progeny.

It is yet another object of the present invention to disclose the method as defined above, comprising an additional step of selfing at least once the F2 progeny to produce F3 plants and further selecting at least one tomato plant exhibiting a branching inflorescence phenotype, wherein the plant produces statistically significant high yield of mature fruits having the characteristics of average individual fruit weight or average individual fruit brix levels or a combination thereof, similar to fruits produced by a tomato line that is used as the normally branched parent line of the tomato plant.

It is yet another object of the present invention to disclose the method as defined above, comprising an additional step of backcrossing at least once the F1 and/or the F2 plants with at least one normally branched parental line, or elite line or breeding tomato line, and selecting at least one tomato plant exhibiting a branching inflorescence phenotype, wherein the plant produces statistically significant high yield of mature fruits having the characteristics of average individual fruit weight or average individual fruit brix levels or a combination thereof, similar to fruits produced by a tomato line that is used as the normally branched parent line of the tomato plant.

It is yet another object of the present invention to disclose the method as defined above, comprising an additional step of introducing into the genome of the plant at least one trait selected from the group consisting of: high germination rate, vigorous growth, herbicide resistance, insect resistance, resistance to bacterial, fungal or viral disease, resistance to non biotic stress and any combination thereof.

It is yet another object of the present invention to disclose the method as defined above, comprising an additional step of repeating the step of crossing and the step of selecting at least once.

It is yet another object of the present invention to disclose a tomato plant and parts thereof produced by the method as defined above.

It is yet another object of the present invention to disclose a method for screening for a tomato plant exhibiting a branching inflorescence phenotype comprising the steps of: screening the genome of the plant for the presence of a molecular marker combination selected from the group consisting of: a single nucleotide polymorphism at the position corresponding to position 2,313 in SEQ ID NO:7 combined with a 271 bp indel marker having a nucleotide sequence corresponding to the nucleotide sequence as set forth in SEQ ID NO:5, and a single nucleotide polymorphism at the position corresponding to position 1,589 in SEQ ID NO:7 combined with a 271 bp indel marker having a nucleotide sequence corresponding to the nucleotide sequence as set forth in SEQ ID NO:5; and a combination thereof; the molecular marker combination co-segregates with a branching inflorescence phenotype;

wherein the presence of at least one molecular marker combination selected from a group consisting of: (a) T or A at the position corresponding to position 2,313 of SEQ ID NO:7 combined with a deletion of a 271 bp indel marker having a nucleotide sequence corresponding to the nucleotide sequence as set forth in SEQ ID NO:5, (b) C or G at the position corresponding to position 2,313 of SEQ ID NO:7 combined with the presence of a 271 bp indel marker having a nucleotide sequence corresponding to the nucleotide sequence as set forth in SEQ ID NO:5, (c) T or A at the position corresponding to position 1,589 of SEQ ID NO:7 combined with a deletion of a 271 bp indel marker having a nucleotide sequence corresponding to the nucleotide sequence as set forth in SEQ ID NO:5, and (d) T or A at the position corresponding to position 1,589 of SEQ ID NO:7 combined with the presence of a 271 bp indel marker having a nucleotide sequence corresponding to the nucleotide sequence as set forth in SEQ ID NO:5; is indicative of a plant having a branching inflorescence phenotype.

It is yet another object of the present invention to disclose method for identifying haplotypes associated with a branching inflorescence phenotype, the method comprising the steps of: (a) isolating a DNA sample from a tomato plant; (b) analyzing the DNA for the presence of at least one molecular marker combination selected from the group consisting of: (i) a single nucleotide polymorphism at the position corresponding to position 2,313 in SEQ ID NO:7 combined with a 271 bp indel marker having a nucleotide sequence corresponding to the nucleotide sequence as set forth in SEQ ID NO:5, and (ii) a single nucleotide polymorphism at the position corresponding to position 1,589 in SEQ ID NO:7 combined with a 271 bp deletion marker having a nucleotide sequence corresponding to the nucleotide sequence as set forth in SEQ ID NO:5;

wherein the presence of at least one molecular marker combination selected from a group consisting of: (a) T or A at the position corresponding to position 2,313 of SEQ ID NO:7 combined with a deletion of a 271 bp indel marker having a nucleotide sequence corresponding to the nucleotide sequence as set forth in SEQ ID NO:5, (b) C or G at the position corresponding to position 2,313 of SEQ ID NO:7 combined with the presence of a 271 bp indel marker having a nucleotide sequence corresponding to the nucleotide sequence as set forth in SEQ ID NO:5, (c) T or A at the position corresponding to position 1,589 of SEQ ID NO:7 combined with a deletion of a 271 bp indel marker having a nucleotide sequence corresponding to the nucleotide sequence as set forth in SEQ ID NO:5, and (d) T or A at the position corresponding to position 1,589 of SEQ ID NO:7 combined with the presence of a 271 bp indel marker having a nucleotide sequence corresponding to the nucleotide sequence as set forth in SEQ ID NO:5; is indicative of a plant having a branching inflorescence phenotype;

wherein the at least one molecular marker combination co-segregates with a branching inflorescence phenotype, further wherein the analysis is configured to discriminate between normally branching inflorescence phenotype and branching inflorescence phenotypes having distinct haplotype.

It is yet another object of the present invention to disclose the method as defined above, wherein the plant comprising within its genome at least one molecular marker combination selected from the group consisting of: (a) T or A at the position corresponding to position 2,313 of SEQ ID NO:7 combined with a deletion of a 271 bp indel marker having a nucleotide sequence corresponding to the nucleotide sequence as set forth in SEQ ID NO:5, and (b) T or A at the position corresponding to position 1,589 of SEQ ID NO:7 combined with a deletion of a 271 bp indel marker having a nucleotide sequence corresponding to the nucleotide sequence as set forth in SEQ ID NO:5; is obtainable from a tomato plant *Solanum lycopersicum* HAG1, grown from seeds deposited with NCIMB Aberdeen AB21 9YA, Scotland, UK on Apr. 11, 2012 under accession number NCIMB 41958 and from progenies thereof.

It is yet another object of the present invention to disclose the method as defined above, wherein the plant comprising within its genome at least one molecular marker combination selected from the group consisting of: (a) C or G at the position corresponding to position 2,313 of SEQ ID NO:7 combined with the presence of a 271 bp indel marker having a nucleotide sequence corresponding to the nucleotide sequence as set forth in SEQ ID NO:5, and (b) T or A at the position corresponding to position 1,589 of SEQ ID NO:7 combined with the presence of a 271 bp indel marker having a nucleotide sequence corresponding to the nucleotide sequence as set forth in SEQ ID NO:5; is obtainable from *Solanum lycopersicum* 4468, grown from seeds deposited with NCIMB Aberdeen AB21 9YA, Scotland, UK on Apr. 11, 2012 under accession number NCIMB 41957 and from progenies thereof.

It is yet another object of the present invention to disclose a method for detecting a tomato plant exhibiting a branching inflorescence phenotype, wherein the plant produces statistically significant high yield of mature fruits having the characteristics of average individual fruit weight or average individual fruit brix levels or a combination thereof, similar to fruits produced by a tomato line that is used as the normally branched parent line of the tomato plant, the method comprising the steps of (a) isolating a genomic DNA sample form the plant; (b) analyzing the DNA for the presence of at least one molecular marker selected from the group consisting of: a 271 bp deletion marker having a nucleotide sequence corresponding to the nucleotide sequence as set forth in SEQ ID NO:5, a single nucleotide polymorphism at the position corresponding to position 2197 in SEQ ID NO:6, a single nucleotide polymorphism at the position corresponding to position 2,313 in SEQ ID NO:7, a single nucleotide polymorphism at the position corresponding to position 1,589 in SEQ ID NO:7 and a combination of a single nucleotide polymorphism at the position corresponding to position 2,161 in SEQ ID NO:7 and a single nucleotide polymorphism at the position corresponding to position 2,146 in SEQ ID NO:7, the at least one molecular marker is co-segregating with a branching inflorescence phenotype; (c) selecting at least one plant having the characteristics of step (b); and, (d) evaluating fruit yield parameters of the at least one selected plant of step (c), and selecting at least one plant producing statistically significant high yield of mature fruits having the characteristics of average individual fruit weight or average individual fruit brix levels or a combination thereof, similar to fruits produced by a tomato line that is used as the normally branched parent line of the tomato plant.

It is yet another object of the present invention to disclose the method as defined above, further comprising additional steps of: (a) amplifying a DNA segment using a first primer having a polynucleotide sequence as set forth in SEQ ID NO:1 and a second primer having a polynucleotide sequence as set forth in SEQ ID NO:2; and, (b) analyzing the amplified DNA segments produced by the amplification of step (a), wherein the presence of a DNA segment having a polynucleotide sequence corresponding to the sequence as set forth in SEQ ID NO:3 and a DNA segment having a polynucleotide sequence corresponding to the sequence as set forth in SEQ ID NO:4, is indicative of a plant having a branching inflorescence phenotype, wherein the plant produces statistically significant high yield of mature fruits having the characteristics of average individual fruit weight or average individual fruit brix levels or a combination thereof, similar to fruits produced by a tomato line that is used as the normally branched parent line of the tomato plant.

It is yet another object of the present invention to disclose an oligonucleotide primer pair having the sequence as set forth in SEQ ID NO:1 and SEQ ID NO:2, wherein the sequences are suitable for the detection of a tomato plant exhibiting a branching inflorescence phenotype, wherein the plant produces statistically significant high yield of mature fruits having the characteristics of average individual fruit weight or average individual fruit brix levels or a combination thereof, similar to fruits produced by a tomato line that is used as the normally branched parent line of the tomato plant.

It is yet another object of the present invention to disclose an isolated nucleotide sequence having at least 90% sequence identity with the sequence selected from a group consisting of at least one of the nucleotide sequences corresponding to the nucleotide sequences as set forth in: SEQ ID NO:3, SEQ ID NO:4 and SEQ ID NO:5 and any combination thereof, wherein the sequences are suitable for the detection of a tomato plant exhibiting a branching inflorescence phenotype, wherein the plant produces statistically significant high yield of mature fruits having the characteristics of average individual fruit weight or average individual fruit brix levels or a combination thereof, similar to fruits produced by a tomato line that is used as the normally branched parent line of the tomato plant.

It is yet another object of the present invention to disclose the use of a single nucleotide polymorphism or a polynucleotide sequence selected from a group consisting of: a 271 bp deletion marker having a nucleotide sequence corresponding to the nucleotide sequence as set forth in SEQ ID NO:5, a single nucleotide polymorphism at the position corresponding to position 2197 in SEQ ID NO:6, a single nucleotide polymorphism at the position corresponding to position 2,313 in SEQ ID NO:7, a single nucleotide polymorphism at the position corresponding to position 1,589 in SEQ ID NO:7 and a combination of a single nucleotide polymorphism at the position corresponding to position 2,161 in SEQ ID NO:7 and a single nucleotide polymorphism at the position corresponding to position 2,146 in SEQ ID NO:7 and any combination thereof, in marker based selection of a tomato plant exhibiting a branching inflorescence phenotype, wherein the plant produces statistically significant high yield of mature fruits having the characteristics of average individual fruit weight or average individual fruit brix levels or a combination thereof, similar to fruits produced by a tomato line that is used as the normally branched parent line of the tomato plant.

It is yet another object of the present invention to disclose the use of a single nucleotide polymorphism or polynucleotide sequence selected from a group consisting of: (a) a single nucleotide polymorphism at the position corresponding to position 2,313 in SEQ ID NO:7 combined with a 271 bp indel marker having a nucleotide sequence corresponding to the nucleotide sequence as set forth in SEQ ID NO:5, and (b) a single nucleotide polymorphism at the position corresponding to position 1,589 in SEQ ID NO:7 combined with a 271 bp indel marker having a nucleotide sequence corresponding to the nucleotide sequence as set forth in SEQ ID NO:5; in marker based selection of a tomato plant having a branching inflorescence phenotype.

BRIEF DESCRIPTION OF THE FIGURES

In order to understand the invention and to see how it may be implemented in practice, a plurality of preferred embodiments will now be described, by way of non-limiting example only, with reference to the accompanying Figures, wherein.

DETAILED DESCRIPTION OF THE INVENTION

Figure 1:
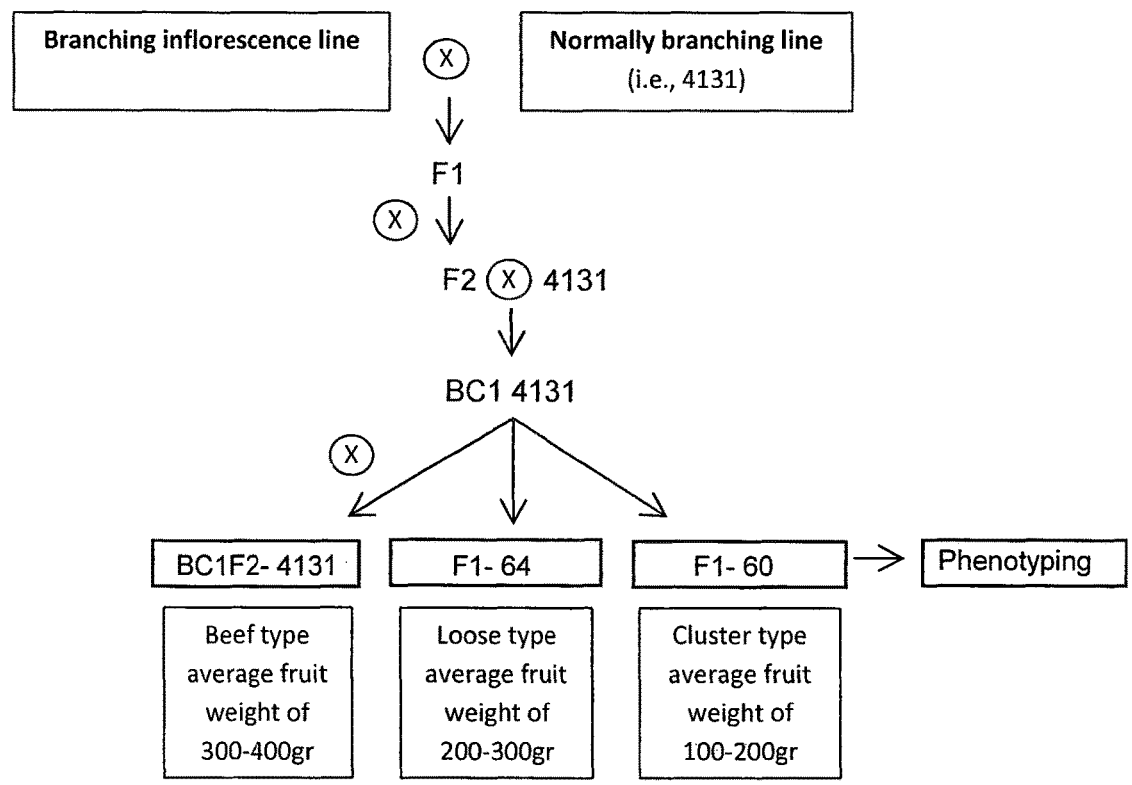
FIG. 1 is illustrating a breeding scheme of a branching inflorescence phenotype introgression into a normally branched commercial tomato lines of three genetic backgrounds.

The following description is provided, alongside all chapters of the present invention, so as to enable any person skilled in the art to make use of said invention and sets forth the best modes contemplated by the inventor of carrying out this invention. Various modifications, however, is adapted to remain apparent to those skilled in the art, since the generic principles of the present invention have been defined specifically to provide tomato plants exhibiting high yield characteristics.

The present invention relates to the production of tomato plants capable of producing a crop of a commercial value.

A major parameter in commercial success of tomato varieties is directed towards increasing the fruit yield. The present invention addresses this need by exploitation of the variation in the branching of tomato inflorescences, which determines flower number. Although highly branched tomato plants are known to produce small fruits, it is herein shown that the variation in the branching of plant inflorescences is surprisingly associated with reproductive success and crop yield. By introgression of a branching inflorescence trait into a potentially commercially valuable tomato strain, the number of potential fruits per cluster is increased, surprisingly, without the expense of decreasing individual fruit weight; as a result, the fruit weight yield is increased.

According to a further aspect of the invention, heterozygous configuration of the branching inflorescence trait is herein demonstrated to confer at least one heterotic phenotypic effect with respect to the increased fruit yield characteristics of the tomato plants of the present invention. It is submitted that in a core aspect of the invention, the heterosis effect of the hybrids is unpredictable. The heterozygous configuration of the branching inflorescence trait is shown to reduce branching but unexpectedly to increase tomato yield, with no effect on fruit size and/or fruit brix values.

Thus, it is one object of the present invention to provide a tomato plant exhibiting a branching inflorescence phenotype, wherein said plant produces statistically significant high yield of mature fruits having the characteristics of average individual fruit weight or average individual fruit brix levels or a combination thereof, similar to fruits produced by a tomato line that is used as the normally branched parent line of said tomato plant.

Definitions

The technical terms and expressions used within the scope of this application are generally to be given the meaning commonly applied to them in the pertinent art of plant breeding and cultivation if not otherwise indicated herein below.

As used herein the term "about" denotes ±25% of the defined amount or measure or value.

As used herein the term "similar" denotes a correspondence or resemblance range of about ±20%, particularly ±15%, more particularly about ±10% and even more particularly about ±5%.

As used herein the term "average" refers to the mean value as obtained by measuring a predetermined parameter in each plant of a certain plant population and calculating the mean value according to the number of plants in said population.

Figure 2:
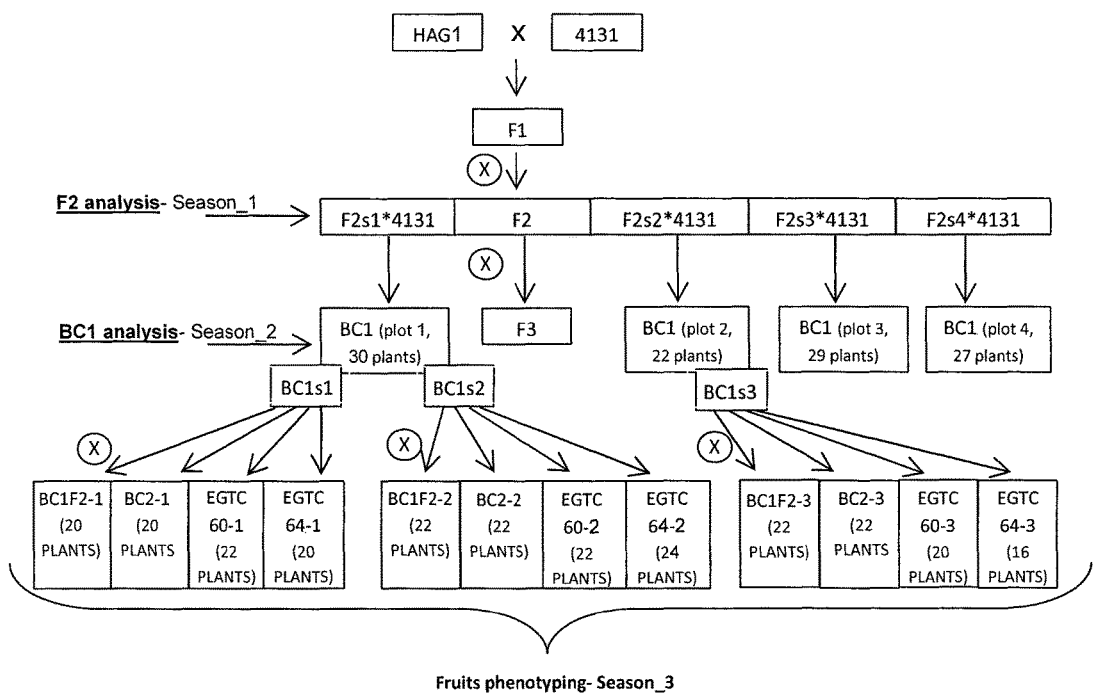
FIG. 2 is illustrating a scheme describing pedigrees and selection steps as embodiments of the present invention used to produce the significantly high yield tomato plants.

According to certain embodiments of the invention, the average value of yield parameters such as fruit yield per plant and fruit yield per cluster can be calculated by measuring the selected parameter in each plant of a selected plant population having the same genetic background (i.e. BC1F2, BC2, EGTC-60 or EGTC-64 populations of FIGS. 1 and 2). The sum of the individual obtained results can then be, divided by the number of plants in the specific population.

According to other embodiments of the invention, the average individual fruit weight and average individual fruit brix values can be determined by calculating an average value of 10 independently measured matured fruits picked from the same plant. The average individual fruit weight and average individual fruit brix values of a certain plant population refers to the mean value as determined by calculating the sum of the average value per plant of the measured plants in said plant population and dividing it by the number of plants in the population.

As used in this specification and the appended claims, the singular forms "a", "an", and "the" include plural referents unless the context clearly dictates otherwise. Thus, for example, reference to "a plant" includes one or more plants, and reference to "a cell" includes mixtures of cells, tissues, and the like.

A "plant" as used herein refers to any plant at any stage of development, particularly a seed plant.

The term "plant" includes the whole plant or any parts or derivatives thereof, such as plant cells, plant protoplasts, plant cell tissue culture from which tomato plants can be regenerated, plant callus or calli, meristematic cells, microspores, embryos, immature embryos, pollen, ovules, anthers, fruit (e.g. harvested tomato fruit), flowers, leaves, cotyledons, pistil, seeds, seed coat, roots, root tips and the like.

The term "plant cell" used herein refers to a structural and physiological unit of a plant, comprising a protoplast and a cell wall. The plant cell may be in a faun of an isolated single cell or a cultured cell, or as a part of higher organized unit such as, for example, plant tissue, a plant organ, or a whole plant.

The term "plant cell culture" as used herein means cultures of plant units such as, for example, protoplasts, regenerable cells, cell culture, cells, cells in plant tissues, pollen, pollen tubes, ovules, embryo sacs, zygotes and embryos at various stages of development, leaves, roots, root tips, anthers, meristematic cells, microspores, flowers, cotyledons, pistil, fruit, seeds, seed coat or any combination thereof.

The term "plant material" or "plant part" used herein refers to leaves, stems, roots, root tips, flowers or flower parts, fruits, pollen, egg cells, zygotes, seeds, seed coat, cuttings, cell or tissue cultures, or any other part or product of a plant or a combination thereof.

A "plant organ" as used herein means a distinct and visibly structured and differentiated part of a plant such as a root, stem, leaf, flower, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture, protoplasts, meristematic cells, calli and any group of plant cells organized into structural and/or functional units. The use of this term in conjunction with, or in the absence of, any specific type of plant tissue as listed above or otherwise embraced by this definition is not intended to be exclusive of any other type of plant tissue.

As used herein, the term "population" means a genetically heterogeneous collection of plants sharing a common genetic derivation.

As used herein, the term "progeny" or "progenies" refers in a non limiting manner to offspring or descendant plants. According to certain embodiments, the term "progeny" or "progenies" refers to plants developed or grown or produced from the deposited seeds as detailed inter alia. The plants grown from the deposited seeds preferably have the desired traits of the deposited seeds, i.e. a branching inflorescence phenotype.

As used herein, the term "tomato plant" refers to a plant of the genus *Solanum*, preferably to plants of the species *Solanum lycopersicum*.

The term "tomato" as used herein refers to any variety, cultivar, or population of *Solanum lycopersicum* including, but not limited to var. cerasiforme, *Solanum pimpinellifolium, Solanum cheesmaniae, Solanum neorickii, Solanum chmielewskii, Solanum habrochaites, Solanum pennellii, Solanum peruvianum, Solanum chilense, S. lycopersicoides, S. N peruvianum, S. corneliomuelleri, S. 'Callejon de Huaylas', S. galapagense* a.d *S. sitiens*. and *Solanum lycopersicum*.

The term "tomato product" used herein refers to any food products and beverages whose primary ingredients are tomato fruits. For example, prepared or processed tomato fruits or product (whole or in pieces), tomato puree or tomato paste, tomato juice, mixtures of vegetable juice, tomato ketchup, tomato sauce or any combination thereof.

The term "mature fruits" used herein refers to sufficiently developed or ripen tomato fruit. According to certain aspects of the invention, such fruits are mature enough to be eaten or used. In specific embodiments, "mature fruits" refers to tomato fruits having red pigments, or fruits that reached breaker stage, referred to as stage two of the ripening process, in which there may be an obvious break in the color of the tomato. The coloring may be pink or red preferably not on more than 10 percent of the tomato fruit surface.

According to preferred embodiments, the tomato plants as disclosed by the present invention produce statistically significant high yield of mature fruits characterized by having individual fruit weight and fruit brix levels that are similar to the corresponding parameters of fruits produced by a tomato line that is used as the normal or regular branched parent line of said tomato plant.

The term "variety" or "cultivar" used herein means a group of similar plants that by structural features and performance can be identified from other varieties within the same species.

The term "genetic background" used herein refers to any inbreeding group, including taxonomic subgroups such as subspecies, taxonomically subordinate to species and superordinate to a race or subrace and marked by a pre-determined profile of latent factors of hereditary traits.

Tomato genetic backgrounds used in the present invention include, but are not limited to tomato varieties having fruit types such as slicing or globe shaped tomatoes, cherry tomatoes, beef or beefsteak tomatoes, plum tomatoes, cluster type tomatoes and loose type tomatoes. The tomato genetic backgrounds used in the present invention may be of a staking or indeterminate variety, bush or determinate variety or of the vigorous bush or semi determinate variety.

The term "allele(s)" used herein means any of one or more alternative or variant forms of a gene or a genetic unit at a particular locus, all of which alleles relate to one trait or characteristic at a specific locus. In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus. Such alternative or variant forms of alleles may be the result of single nucleotide polymorphisms, insertions, inversions, translocations or deletions, or the consequence of gene regulation caused by, for example, by chemical or structural modification, transcription regulation or post-translational modification/regulation.

An allele associated with a qualitative trait may comprise alternative or variant forms of various genetic units including those that are identical or associated with a single gene or multiple genes or their products or even a gene disrupting or controlled by a genetic factor contributing to the phenotype represented by the locus.

As used herein, the term "locus" (loci plural) means a specific place or places or region or a site on a chromosome where for example a gene or genetic marker element or factor is found. In specific embodiments, such a genetic element is contributing to a trait.

As used herein, the term "breeding", and grammatical variants thereof, refer to any process that generates a progeny individual. Breeding can be sexual or asexual, or any combination thereof. Exemplary non-limiting types of breeding include crossing, introgressing, selfing, backcrossing, doubled haploid derivative generation, and combinations thereof.

The term "backcrossing" used herein is understood within the scope of the invention to refer to a process in which a hybrid progeny is repeatedly crossed back to one of the parents. Such a backcrossing process refers to the repeated crossing of a hybrid progeny back to one of the parental tomato plants. The parental tomato plant, which contributes the gene for the desired characteristic, is termed the nonrecurrent or donor parent. This terminology refers to the fact that the nonrecurrent parent is used one time in the backcross protocol and therefore does not recur. The parental tomato plant to which the gene or genes from the nonrecurrent parent are transferred is known as the recurrent parent as it is used for several rounds in the backcrossing protocol. In a typical backcross protocol, a plant from the original varieties of interest (recurrent parent) is crossed to a plant selected from second varieties (nonrecurrent parent) that carries the single gene of interest to be transferred. The resulting progeny from this cross are then crossed again to the recurrent parent and the process is repeated until a tomato plant is obtained wherein essentially all of the desired morphological and physiological characteristics of the recurrent parent are recovered in the converted plant, in addition to the single transferred gene from the nonrecurrent parent. Backcrossing methods can be used with the present invention to improve or introduce a characteristic into the parent lines It is also within the scope of the invention that backcrossing refers to a system for incorporating desirable inherited traits into an elite or breeding line. In such a system, the "donor parent" refers to the line containing the gene or trait of interest and the recipient parent or recurrent parent refers to the tomato line that is used as the normal or regular branched parent line, which is preferably an elite or breeding plant line that is improved by adding the gene or trait of interest.

Examples of populations produced by a backcross used within the scope of the present invention include, but are not limited to 'BC1' population relating to the progeny plants of a backcross between F2 generation plants and the recipient parental line (i.e. line 4131), 'BC1F2' population relating to the progeny produced by self pollination of the 'BC1' plants, and 'BC2' population relating to the progeny of a backcross between the 'BC1' population and the recipient parental line (i.e. line 4131).

It is noted that different tomato lines, used as the normally branched parent line or recurrent parents may be used in subsequent backcrosses. For example, the term "early generation test cross" or "EGTC" used herein refers to a cross between a BC1 population plant and a tomato plant having a genetic background, which is different from the genetic background of the recipient parental line. A recipient line may be 4131, characterized by producing beefsteak type tomatoes. Examples of plant populations resulting from EGTCs used in the present invention include, but are not limited to, 'EGTC-64' population referring to a cross between a BC1 plant and a plant having loose type tomatoes (i.e. line 64); and 'EGTC-60' population referring to a cross between a BC1 plant and a plant having cluster type tomatoes (i.e. line 60). Examples of genetic backgrounds used in the present invention and their phenotypic description according to UPOV guidelines for the conduct of tests for Distinctness, Uniformity and Stability (DUS) directed to tomato *Lycopersicon lycopersicum* (TG/44/10) are presented in Table 2.

The present invention also relates to seeds harvested from the F1 hybrid tomato plants derived of any cross described herein, and plants grown from these seeds. A common practice in plant breeding is using the method of backcrossing to develop new varieties by genetic determinant introgression.

The term "genetic determinant introgression" as used herein refers to the incorporation of new genetic determinants such as genes, alleles, QTLs or traits, into a line wherein essentially all of the desired morphological and physiological characteristics of the line are recovered, in addition to the genetically introgressed determinant. Such a process is often used in cultivar development, in which one or a few genetic determinants are transferred to a desired genetic background, preferably by using backcrossing.

The term "transformation" used herein refers to genetic alteration or modification induced by the introduction of exogenous DNA into a cell. This includes both integration of the exogenous DNA into the host genome, and/or introduction of plasmid DNA containing the exogenous DNA into the plant cell. Such a transformation process results in the uptake, incorporation and expression of exogenous genetic material (exogenous DNA). Plant transformation may refer to the introduction of exogenous genes into plant cells, tissues or organs employing direct or indirect means developed by molecular and cellular biology.

As used herein, the term "co-segregate" is understood within the scope of the invention to refer to the tendency for genes, traits and/or genetic markers to segregate or to be inherited together. In a specific embodiment, the presence of a molecular or genetic marker within the genome of the plant is associated with the presence of a trait or a phenotype of the plant, i.e. a branching inflorescence phenotype. Alternatively, two or more genes, gene alleles or genetic markers that are linked on the same chromosome are transmitted to the same daughter cell leading to the inheritance by the offspring of these genes or alleles together.

More specifically, in the context of the present invention, the term "co-segregate" refers to the fact that the allele for the trait and the allele(s) for the marker(s) tend to be transmitted together because they are on the same chromosome, and reduced recombination between them resulting in a non-random association of their alleles on the same chromosome. "Co-segregation" also refers to the presence of two or more traits, genetic markers or combinations thereof, within a single plant of which at least one is known to be genetic and which cannot be readily explained by chance. In some embodiments, novel genetic markers are herein identified to co segregate with the branching inflorescence trait or phenotype.

The term "co-segregate" used in the present invention is analogous to coupling or co-inheriting in some of the embodiments of the invention.

As used herein, the term "trait" refers to characteristic or phenotype. A phenotypic trait may refer to the appearance or other detectable characteristic of an individual, resulting from the interaction of its genome, proteome and/or metabolome with the environment. For example, in the context of the present invention a branching inflorescence trait relates to the pattern in which the flowers are organized on the tomato plant as described herein. A trait may be inherited in a dominant or recessive manner, or in a partial or incomplete-dominant manner. A trait may be monogenic (i.e. determined by a single locus) or polygenic (i.e. determined by more than one locus) or may also result from the interaction of one or more genes with the environment. A dominant trait results in a complete phenotypic manifestation at heterozygous or homozygous state; conventionally, a recessive trait manifests itself only when present at homozygous state.

It is within the scope of the present invention that the term "non-recessive inheritance" used herein after refers to inheritance in a manner in which mutations in one copy of the gene or one allele is sufficient to cause a phenotypic effect. A non recessive inheritance within the scope of the present invention may include a dominant inheritance, a co dominant inheritance and an incomplete dominance or an incomplete dominant inheritance.

The term "incomplete dominance" used hereinafter refers to a type of inheritance in which the heterozygote has a phenotype intermediate to those of the homozygous parents.

As used herein, the term "homozygous" refers to a genetic condition or configuration existing when two identical or like alleles reside at a specific locus, but are positioned individually on corresponding pairs of homologous chromosomes in the cell of a diploid organism.

Conversely, as used herein, the term "heterozygous" means a genetic condition or configuration existing when two different or unlike alleles reside at a specific locus, but are positioned individually on corresponding pairs of homologous chromosomes in the cell of a diploid organism. In specific embodiments, the tomato plants of the present invention comprise heterozygous configuration of the genetic markers associated with the high yield characteristics.

A "cultivated tomato" plant is understood within the scope of the invention to refer to a plant that is no longer in the natural state but has been developed by human care and for human use and/or growing purposes and/or consumption. "Cultivated plants" are further understood to exclude those wild-type species, which comprise the trait being subject of this invention as a natural trait and/or part of their natural genetics.

As used herein, the phrase "diploid individual" or "diploid organism" refers to an individual that has two sets of chromosomes, typically one from each of its two parents. However, it is understood that in some embodiments a diploid individual can receive its "maternal" and "paternal" sets of chromosomes from the same single organism, such as when a plant is selfed to produce a subsequent generation of plants.

"Genetic linkage" is understood within the scope of the invention to refer to an association of characters in inheritance due to location of genes in proximity on the same chromosome, measured by percent recombination between loci (centi-Morgan, cM).

As used herein, the phrases "sexually crossed" and "sexual reproduction" in the context of the presently disclosed subject matter refers to the fusion of gametes to produce progeny (e.g., by fertilization, such as to produce seed by pollination in plants). A "sexual cross" or "cross-fertilization" is in some embodiments fertilization of one individual by another (e.g., cross-pollination in plants).

The term "selfing" used herein refers in some embodiments to the production of seed by self-fertilization or self-pollination; i.e., pollen and ovule are from the same plant.

As used herein, the phrase "genetic marker" or "molecular marker" or "biomarker" refers to a feature in an individual's genome e.g., a nucleotide or a polynucleotide sequence that is associated with one or more loci or trait of interest. In some embodiments, a genetic marker is polymorphic in a population of interest, or the locus occupied by the polymorphism, depending on context. Genetic markers or molecular markers include, for example, single nucleotide polymorphisms (SNPs), indels (i.e., insertions/deletions), simple sequence repeats (SSRs), restriction fragment length polymorphisms (RFLPs), random amplified polymorphic DNAs (RAPDs), cleaved amplified polymorphic sequence (CAPS) markers, Diversity Arrays Technology (DArT) markers, and amplified fragment length polymorphisms (AFLPs) or combinations thereof, among many other examples such as the DNA sequence per se. Genetic markers can, for example, be used to locate genetic loci containing alleles on a chromosome that contribute to variability of phenotypic traits. The phrase "genetic marker" or "molecular marker" or "biomarker" can also refer to a polynucleotide sequence complementary or corresponding to a genomic sequence, such as a sequence of a nucleic acid used as a probe or primer.

A genetic marker can be physically located in a position on a chromosome that is within or outside of the genetic locus with which it is associated (i.e., is intragenic or extragenic, respectively). In some embodiments of the presently disclosed subject matter, the one or more genetic markers comprise a combination of two or more genetic markers. It is also within the scope of the present invention that different combinations of genetic markers are used to identify different traits or phenotypic characteristics as disclosed inter alia.

The term "genotype" refers to the genetic constitution of a cell or organism. An individual's genotype includes the specific alleles, for one or more genetic marker loci, present in the individual's haplotype. As is known in the art, a genotype can relate to a single locus or to multiple loci, whether the loci are related or unrelated and/or are linked or unlinked. In some embodiments, an individual's genotype relates to one or more genes that are related in that the one or more of the genes are involved in the expression of a phenotype of interest. Thus, in some embodiments a genotype comprises a summary of one or more alleles present within an individual at one or more genetic loci. In some embodiments, a genotype is expressed in terms of a haplotype.

The term "haplotype" used herein refers hereinafter generally to a combination of alleles (DNA sequences) at adjacent locations (loci) on a chromosome that are transmitted together. A haplotype may be one locus, several loci, or an entire chromosome depending on the number of recombination events that have occurred between a given set of loci. The term "haplotype" further refers to a set of single-nucleotide polymorphisms (SNPs) on a single chromosome of a chromosome pair that are associated statistically.

As used herein, the term "germplasm" refers to the totality of the genotypes of a population or other group of individuals (e.g., a species). The term "germplasm" can also refer to plant material; e.g., a group of plants that act as a repository for various alleles. Such germplasm genotypes or populations include plant materials of proven genetic superiority; e.g., for a given environment or geographical area, and plant materials of unknown or unproven genetic value; that are not part of an established breeding population and that do not have a known relationship to a member of the established breeding population.

The terms "hybrid", "hybrid plant" and "hybrid progeny" used herein refers to an individual produced from genetically different parents (e.g., a genetically heterozygous or mostly heterozygous individual).

As used herein, the phrase "inbred line" refers to a genetically homozygous or nearly homozygous population. An inbred line, for example, can be derived through several cycles of brother/sister breedings or of selfing or in dihaploid production. In some embodiments, inbred lines breed true for one or more phenotypic traits of interest.

As used herein, the term "dihaploid line", refers to stable inbred lines issued from pollen or egg cells or other cells of the gametophyte. A dihaploid occurs as a result of a spontaneous or induced chromosome doubling in haploid cells during embryogenesis. "Dihaploid" plants are essentially not segregating any more (stable).

As used herein, the term "linkage", and grammatical variants thereof, refers to the tendency of alleles at different loci on the same chromosome to segregate together more often than would be expected by chance, if their transmission were independent, in some embodiments as a consequence of their physical proximity.

The term "corresponding to the nucleotide sequence" refers to sequence homology or sequence identity. These terms relate to two or more nucleic acid or protein sequences, that are the same or have a specified percentage of amino acid residues or nucleotides that are the same, when compared and aligned for maximum correspondence, as measured using one of the available sequence comparison algorithms or by visual inspection. If two sequences, which are to be compared with each other, differ in length, sequence identity preferably relates to the percentage of the nucleotide residues of the shorter sequence, which are identical with the nucleotide residues of the longer sequence. As used herein, the percent of identity or homology between two sequences is a function of the number of identical positions shared by the sequences, taking into account the number of gaps, and the length of each gap, which needs to be introduced for optimal alignment of the two sequences. The comparison of sequences and determination of identity percent between two sequences can be accomplished using a mathematical algorithm as known in the relevant art. According to further aspects of the invention, the term "corresponding to the nucleotide sequence", refers to variants, homologues and fragments of the indicated nucleotide sequence which possess or perform the same biological function or correlates with the same phenotypic characteristic of the indicated nucleotide sequence.

Another indication that two nucleic acid sequences are substantially identical or that a sequence is "corresponding to the nucleotide sequence" is that the two molecules hybridize to each other under stringent conditions. High stringency conditions, such as high hybridization temperature and low salt in hybridization buffers, permits only hybridization between nucleic acid sequences that are highly similar, whereas low stringency conditions, such as lower temperature and high salt, allows hybridization when the sequences are less similar.

In other embodiments of the invention, such substantially identical sequences refer to polynucleotide or amino acid sequences that share at least about 80% similarity, preferably at least about 90% similarity, alternatively, about 95%, 96%, 97%, 98% or 99% similarity to the indicated polynucleotide or amino acid sequences.

The term "homolog" as used herein, refers to a DNA or amino acid sequence having a degree of sequence similarity in terms of shared amino acid or nucleotide sequences. There may be partial similarity or complete similarity (i.e., identity). For protein sequences, amino acid similarity matrices may be used as are known in different bioinformatics programs (e.g. BLAST, FASTA, Bestfit program—Wisconsin Sequence Analysis Package, Version 8 for Unix, Genetics Computer Group, University Research Park, 575 Science Drive Madison, Wis. 53711, Smith Waterman). Different results may be obtained when performing a particular search with a different matrix. Degrees of similarity for nucleotide sequences are based upon identity matches with penalties made for gaps or insertions required to optimize the alignment, as is well known in the art (e.g. Altschul S. F. et al., 1990, J Mol Biol 215(3):403-10; Altschul S. F. et al., 1997, Nucleic Acids Res. 25:3389-3402). Guidance in determining which amino acid residues may be substituted, inserted, or deleted without abolishing biological or activity may be found using computer programs well known in the art, for example, DNASTAR software.

As used herein, the phrase "resistance" refers to the ability of a plant to restrict the growth and development of a specified pathogen and/or the damage they cause when compared to susceptible plants under similar environmental conditions and pathogen pressure. Resistant plants may exhibit some disease symptoms or damage under pathogen or pest pressure, e.g. fungus, virus, bacterium, whitefly, thrips, spidermites and nematodes.

The term "phenotype" is understood within the scope of the invention to refer to a distinguishable characteristic(s) of a genetically controlled trait.

As used herein, the phrase "phenotypic trait" refers to the appearance or other detectable characteristic of an individual, resulting from the interaction of its genome, proteome and/or metabolome with the environment.

The term "polymorphism" is understood within the scope of the invention to refer to the presence in a population of two or more different forms of a gene, genetic marker, or inherited trait or a gene product obtainable, for example, through alternative splicing, DNA methylation, etc.

The term "inflorescence" used herein refers to an arrangement of flowers on the stem of the plant. There are many different types of inflorescences, each with the florets arranged differently from the other types.

Examples of inflorescence types include, but are not limited to, a spike which is a group of flowers arising from the main stem, without individual flower stalks (sessile). An umbel arrangement which is a flower head in which all the flower stalks are of the same length, so that the flower head is rounded like an umbrella. The florets on the outside of the umbel bloom first. A compound umbel is an umbel where each stalk of the umbel produces a smaller umbel of flowers. A cyme is a group of flowers in which the end of each growing point produces a flower, so new growth comes from side shoots and the oldest flowers are at the top. A uniparous cyme is solitary flower with a stem projecting from under it. Florets are connected to this stem by pedicels. A biparous cyme is the same as a uniparous cyme, only it has two stems coming out from under the solitary flower. A raceme is a flower spike where the flowers have stalks of equal length coming from one axis which is the main stem of the inflorescence. In this arrangement, the tip of the stem continues to grow and produce more flowers. Flowers open from the bottom up. A panicle is a branched raceme, each branch having a smaller raceme of flowers. The terminal bud of each branch continues to grow, producing more side shoots and more flowers.

As used herein the term "branching inflorescence phenotype" refers to a complex or compound architecture or pattern or arrangement of inflorescence. In the context of the present invention, a complex inflorescence also refers to compound inflorescences or synflorescences. Compound or complex inflorescences are composed of branched stems and can involve complicated arrangements. Branched inflorescence phenotype is usually determined by measuring number of flowers per inflorescence and fruit or fruit carpel number and mass.

It is herein acknowledged that there are mainly two types of complex inflorescence patterns in tomato. A raceme inflorescence, in which the flowers branch off laterally from a main shoot, that grows indefinitely; and a cymose inflorescence type, in which the shoot apex differentiates into a flower, subsequent growth occurs due to activity in an auxiliary branch, which eventually terminates in a flower. Thus in certain embodiments, cymose inflorescences are determinate, whereas racemose inflorescences or monopodial or indefinite type inflorescences are indeterminate. A cymose or definite type inflorescence can be uniparous (also known as monochasial or sympodial) in which only one lateral branch produced at a time. In other aspects, a cymose type inflorescence may be biparous or dichasial, when two lateral branches develop at a time. Alternatively, a cymose type inflorescence may be multiparous or polychasial when more than two branches develop at a time.

The scope of the term "branching inflorescence" as used herein includes the definition according to the UPOV guidelines for the conduct of tests for Distinctness, Uniformity and Stability (DUS). The UPOV guidelines for tomato *Lycopersicon lycopersicum* (TG/44/10) include definitions relating to inflorescence characteristics, for example, inflorescence type of 2nd and $3^{rd}$ truss.

A "branching inflorescence phenotype" or a "highly branched inflorescence" or a "highly branching inflorescence" is herein defined as mainly multiparous according to UPOV guidelines. In some embodiments of the invention, a plant exhibiting a "highly branching inflorescence phenotype or a "branching inflorescence phenotype", is characterized by having at least 20 flowers per inflorescence or cluster, particularly 50-100 flowers per inflorescence or cluster. One example of such a plant included within the scope of the present invention is the HAG1 genetic source of the branching inflorescence phenotype. Alternatively, a plant exhibiting a "branching inflorescence phenotype" is characterized by having at least 10 flowers per inflorescence. One example of such a plant included within the scope of the present invention is the 4468 genetic source of the branching inflorescence phenotype.

A "normally branched inflorescence" phenotype is herein defined as uniparous i.e. as described for the 4131 elite line, or intermediate, preferably having between about 2 to about 7 flowers per inflorescence i.e. as described for the 4466, 60 and 64 lines. In specific embodiments a "normally branched inflorescence" phenotype also refers to a regularly branched inflorescence or a wild type plant or parent line, lacking the branching inflorescence phenotype or having a regular or normal inflorescence phenotype.

Examples of plants having a "branching inflorescence" phenotype, within the scope of the present invention may include the hybrid plants produced by the crosses as described inter alia. These hybrid tomato plants are defined by the UPOV definitions as having intermediate inflorescence type, preferably having between at least about 7 flowers per inflorescence, particularly about 8 to about 12 flowers per inflorescence. Non limiting examples of hybrid plants or lines or populations within the scope of the present invention are F1, F2, F3, BC2, BC1F2, EGTC64 and EGTC60, 3219 etc. UPOV definitions of plants used in the present invention are detailed in Table 2 as examples of genetic backgrounds and hybrid plants or populations included within the scope of the present invention.

In certain embodiments, the high yield tomato plants of the present invention are characterized by a complicated arrangement of branches, preferably, branched cymes. For example, the flower organization or arrangement may occur in a dichotymously branched cyme. According to specific embodiments, the high yield tomato plants of the present invention have increased number of flowers per cluster and/or per plant relative to a tomato line that is used as the normal or regular branched parent line of said tomato plant. For example, the average number of flowers per cluster of a plant having a branching inflorescence phenotype may vary between about 8 to about 100, a value which is significantly elevated relative to a tomato line that is used as the normal or regular branched parent line of said tomato plant.

It is noted that a potential tomato fruit might be developed from each flower. Thus, it is herein demonstrated that the genetically introgressed tomato plants of the present invention produce elevated number of fruits relative to a tomato line that is used as the normally branched parent line of said tomato plant. These plants are surprisingly characterized by having individual fruit weight and fruit brix levels, which are similar to the fruits produced by their parental lines having normally branched inflorescence.

It is within the scope of the present invention that the "branching inflorescence phenotype" co-segregates or associates with a branching inflorescence trait which is demonstrated by the present invention to be linked with novel set of molecular markers.

One example of a source of a branching inflorescence phenotype that contains the herein described branching inflorescence trait is *Solanum lycopersicum*, line HAG1, grown from seeds deposited with NCIMB Aberdeen AB21 9YA, Scotland, UK on Apr. 11, 2012 under accession number NCIMB 41958. Another example of a source of a branching inflorescence phenotype that contains the herein described branching inflorescence trait is *Solanum lycopersicum*, line 4468, grown from seeds deposited with NCIMB Aberdeen AB21 9YA, Scotland, UK on Apr. 11, 2012 under accession number NCIMB 41957. These and other related tomato plants that exhibit a branching inflorescence phenotype and contain one or more alleles that encode for branching inflorescence phenotype can now be identified by using one or more of the markers provided herein.

In a specific embodiment of the invention, the branching inflorescence trait unexpectedly shows a non-recessive inheritance, particularly incomplete dominant inheritance. It is shown by the present invention that the hybrids produced by crossing a highly branched or a branched inflorescence tomato plant with a plant having a normally branched inflorescence are heterozygous for the trait, unexpectedly characterized by a branching inflorescence phenotype with an average of more than 7 flowers per inflorescence.

The present invention provides new molecular markers disclosed herewith that co-segregate with a branching inflorescence phenotype or trait. In specific embodiments of the invention, the branching inflorescence trait is conferred by at least one "branching inflorescence allele". A "branching inflorescence allele" may include, mutant alleles that co segregate with the genetic markers provided by the present invention According to certain embodiments, the donor of the branching inflorescence trait is a highly branched tomato line producing dozens of flowers per inflorescence.

According to a further embodiment, the tomato plants of the present invention are heterozygous for the branching inflorescence trait or allele. It is a core aspect of the invention that such heterozygous configuration surprisingly and unexpectedly results in at least one heterotic phenotypic effect. The aforementioned effect is characterized by an increased number of fruits per cluster of above 20% and preferably between about 20% to about 80% relative to common elite or breeding tomato lines. A further agricultural advantage of the tomato plants of the present invention is the statistically significant high yield of mature fruits, in contrast to the conventional teaching as described by recent publications (Eshed and Zamir, 1995; Lippman et al, 2008 and Francis, eXtension 2011).

The term "statistically significant high yield" or "high yield" used herein refers to genetically enhanced cultivars of crops such as tomato that have an increased crop production or increased percentage of usable plant parts, preferably fruits. The fruit yield produced by a plant may be affected by parameters such as number of flowers per cluster, number of flowers per plant, number of fruits per plant, individual fruit size or weight, fruit weight per cluster, fruit weight per plant, fruit mass, brix, fruit weight yield per plant, fruit weight yield per cluster, fruit brix*yield, earliness or an average of any of the aforementioned terms or any combination thereof.

According to certain embodiments "statistically significant high yield" or "statistically significant increased yield" or "high yield" refers to an increase of at least about 10%, particularly between about 12% to about 25%, more particularly between about 12% to about 24%, or of at least about 24%, in the average fruit weight per cluster, relative to a tomato line that is used as the normally branched parent line of said tomato plant.

In other embodiments "statistically significant high yield" or "statistically significant increased yield" refers to an increase of at least about 8%, particularly between about 8.5% to about 18%, more particularly between about 10% to about 20%, or of at least about 18%, in the average fruit weight per plant, relative to a tomato line that is used as the normally branched parent line of said tomato plant and/or as compared to a corresponding tomato plant having the same genetic background and lacking the branching inflorescence allele.

In other aspects, the present invention provides tomato plants producing statistically significant high yield of mature fruits with an average individual fruit weight which is surprisingly and unexpectedly similar to the average fruit weight of a tomato line that is used as the normally branched parent line of said tomato plant, or to a reference tomato plant lacking the branching inflorescence trait and having the same genetic background. For example the average individual fruit weight of the statistically significant high yield tomato hybrids of the present invention is in the range of between about 90 gr and about 190 gr.

Thus, the present invention provides tomato plants demonstrating statistically significant increase in the yield of fruit weight, surprisingly, without having the undesirable effect of reduced individual fruit weight. It is hence a main essence of the present invention to provide novel tomato plants with improved yield characteristics of producing statistically significant increased weight of mature fruits having individual fruit weight values similar to the fruits produced by a tomato line that is used as the normal or regular branched parent line of said tomato plant.

In certain aspects of the invention, the term "statistically significant high yield" also refers to the quality of the fruits produced by the tomato plants of the present invention, including fruit characteristics and parameters such as fruit brix, total soluble solids (TSS) content and/or earliness.

As used herein the term "brix" refers to the total soluble solids (TSS) content or soluble solids content (SCC) of a tomato fruit measured in predetermined units, i.e. percentage values or percentage by weight (% w/w) units, whereby one unit of brix denotes about 1 gram of TSS or SCC in 100 gram of fresh weight of tomato fruits. In certain aspects of the invention, soluble solid concentration was measured in the juice of the mature tomato fruit. The measuring may be performed by any conventional method described in the relevant art, for example, according to one embodiment, a few drops were placed on a refractometer and the brix values were read.

According to a certain embodiment, the tomato fruits produced by the statistically high yield tomato plants of the present invention, demonstrate TSS levels of between about 4.0% to about 5.0%. These values are similar to the TSS levels of fruits produced by a common elite or breeding tomato variety used as the normally branched parent and/or similar to a corresponding tomato plant having the same genetic background and lacking the branching inflorescence allele (see Table 5). Fruits having desirable brix levels were demonstrated in hybrids resulting from a cross between a highly branched tomato plant and any tomato line having a normally branched phenotype as exemplified inter alia by lines 60, 64, 4131 or 4466 genetic backgrounds.

As used herein the term "earliness" refers to the rate of fruit development and more specifically to the time elapsing between planting of the seed and the subsequent harvesting. More preferably, it relates to the days from transplanting to first red fruit. Thus, in plants earliness is evaluated by measuring how rapid a state of ripeness is attained. Earliness has economic significance. The cultivation of early ripening plant species and varieties results in a more productive use of land, since the same field may yield more than one harvest per season. The term "earliness" as understood within the context of the present invention relates to varieties for which the time elapsing between planting of the seed and the subsequent harvesting is reduced. An enhanced or increased earliness implies a shorter duration of the growth phase of the plant, which leads to a flowering and a ripening of the fruits to be harvested, which occur, further ahead in time than is normally the case. It is further disclosed that in cultivated tomato, early flowering is generally associated with higher yield of ripe fruits.

The statistically significant high yield tomato plants of the present invention demonstrate enhanced earliness parameters relative to common elite or breeding tomato lines having normally branched inflorescence phenotype. In specific embodiments, the tomato hybrids having the genetic background of line 60, 64, 4131 or 4466 are used as examples of tomato plants or breeding lines that are used, among others for the production of the statistically significant high yield hybrids. These hybrids are herein shown to have an enhanced earliness characteristics i.e. observed by a reduced number of days to first ripen fruit of cluster 6 (C6). In specific embodiments, the demonstrated average increase in earliness, as measured by the decrease in the number of days to first ripen fruit is of at least about 15%, particularly between about 20% and about 50%, more particularly between about 22% and about 35%, relative to the corresponding earliness parameter measured in a tomato line lacking the branching inflorescence trait that is used as the normally branched parent of the hybrid plant.

In a further embodiment, the tomato plants of the present invention are characterized by enhanced earliness without having any deleterious effect on individual fruit weight or other beneficial fruit characteristic such as brix level.

As used herein the term "high germination rate" refers to a germination rate which is elevated by at least 80%, particularly by at least about 90% and more particularly by at least about 95%.

Thus, the present invention provides tomato plants and methods of obtaining them, which are endowed with increasing fruit yield. This is achieved by the novel method of selecting those plants with increased flower number and fruit number without decreased individual fruit weight and/or fruit brix.

The present invention provides tomato plants demonstrating statistically significant increased fruit weight yield surprisingly, without having the undesirable effect of reduced individual fruit weight. The aforementioned unique phenotype is conferred by the revealed heterotic effect of the hybrid plants having heterozygous configuration of a branching inflorescence trait.

In one embodiment, the invention provides tomato plants, particularly cultivated tomato plants, according to any of the preceding embodiments, comprising at least one branching inflorescence trait or allele or genetic determinant, which is obtainable from *Solanum lycopersicum* HAG1, seed of which has been deposited under Deposit Number NCIMB 41958, or in the progeny or in an ancestor thereof, comprising said at least one branching inflorescence trait or a branching inflorescence conferring part thereof.

In another embodiment, the present invention provides a tomato plant, particularly a cultivated tomato plant, according to any of the preceding embodiments comprising a branching inflorescence genetic determinant, which is obtainable from *Solanum lycopersicum* 4468, seed of which has been deposited under Deposit Number NCIMB 41957 or in the progeny or in an ancestor thereof, comprising said at least one branching inflorescence trait or a branching inflorescence conferring part thereof.

The markers provided by the present invention co-segregate with a branching inflorescence trait or allele, obtainable from *Solanum lycopersicum* HAG1, seed of which has been deposited under Deposit Number NCIMB 41958. In other aspects of the invention the molecular markers co-segregate with a branching inflorescence trait or allele, obtainable from *Solanum lycopersicum* 4468, seed of which has been deposited under Deposit Number NCIMB 41957.

Deposits:

The following seed samples of *Solanum lycopersicum* were deposited with NCIMB, Ferguson Building, Craibstone Estate, Bucksburn, Aberdeen AB21 9YA, Scotland, UK on 11 Apr. 2012 under the provisions of the Budapest Treaty in the name of Hazera Genetics Ltd.:

| Accession No. | Date of deposit | *Solanum lycopersicum* seed line designation |
|---|---|---|
| NCIMB 41957 | 11 Apr., 2012 | 4468 |
| NCIMB 41958 | 11 Apr., 2012 | HAG1 |

The aforementioned genomes are obtainable from said deposited material but are also obtainable from other material. The sequence of the genes obtained from other material may vary from the sequence of the gene in the deposited material ("variant"). Deposit Number NCIMB 41957 and 41958 or a genetic variant thereof, which refers essentially the same phenotype are available. Seeds of tomato plants similar to the above, further comprising at least one additional trait selected from the group consisting of high germination rate, herbicide resistance and insect resistance, are obtainable with regard to a deposit made under the Budapest treaty regulations.

Seed samples were deposited with NCIMB, Ferguson Building, Craibstone Estate, Bucksburn, Aberdeen AB21, 9YA, Scotland, UK on 11 Apr. 2012 under the provisions of the Budapest Treaty. The seed samples include accession numbers 41957 and 41958 as designated above.

The aforementioned deposits of the tomato seeds of this invention are maintained by Hazera Genetics Ltd. Mivhor farm M.P. Lachish Darom, Israel. In addition, a sample of the tomato seed of this invention has been deposited by Hazera Genetics Ltd., Mivhor farm M.P. Lachish Darom, Israel with the National Collections of Industrial, Food and Marine Bacteria (NCIMB), 23 St Machar Drive, Aberdeen, Scotland, AB24 3RY, United Kingdom. Hazera Genetics Ltd. has authorized the applicant to refer to the deposited biological material in the application.

The plants of the invention are preferably non-GMO however, it is to be understood that the addition or deletion of traits by transformation is explicitly encompassed within the scope of the invention.

The Tomato Plants of the Present Invention Having the Unique Statistically Significant High Yield Properties According to one embodiment, the present invention provides a tomato plant having a branching inflorescence phenotype, wherein the plant produces statistically significant high yield of mature fruits with average individual fruit weight and/or fruit brix levels similar to fruits produced by a tomato line that is used as the normally branched parent line of the tomato plant.

According to a further embodiment the present invention provides a tomato plant having a genome comprising an introgression derived from a tomato plant having a branching or highly branching inflorescence phenotype, wherein the plant produces statistically significant high yield of mature fruits with average individual fruit weight and fruit brix levels similar to the fruits produced by a tomato line that is used as the normally branched parent line of the tomato plant, the tomato line lacking the introgression.

According to a further embodiment the present invention provides the tomato plant as described above, wherein the plant produces statistically significant high yield of mature fruits as compared to a tomato line that is used as the normally branched parent line of the tomato plant, the tomato line lacking the branching inflorescence phenotype.

According to a further embodiment the present invention provides the tomato plant as described above, wherein the branching inflorescence phenotype is controlled by a genetic determinant which shows a non-recessive inheritance.

According to a further embodiment the present invention provides the tomato plant as described above, wherein the genetic determinant is in a heterozygous configuration.

According to a further embodiment the present invention provides the tomato plant as described above, wherein the heterozygous configuration of the genetic determinant confers at least one heterotic phenotypic effect with respect to the statistically significant high yield of mature fruits.

According to a further embodiment the present invention provides the tomato plant as described above, wherein the genetic determinant shows incomplete dominant inheritance with respect to the branching phenotype.

According to a further embodiment the present invention provides the tomato plant as described above, wherein the branching inflorescence phenotype co-segregates with at least one molecular marker selected from the group consisting of: a 271 bp deletion marker having a nucleotide sequence corresponding to the nucleotide sequence as set forth in SEQ ID NO:5, a single nucleotide polymorphism at the position corresponding to position 2197 in SEQ ID NO:6, a single nucleotide polymorphism at the position corresponding to position 2,313 in SEQ ID NO:7, a single nucleotide polymorphism at the position corresponding to position 1,589 in SEQ ID NO:7 and a combination of a single nucleotide polymorphism at the position corresponding to position 2,161 in SEQ ID NO:7 and a single nucleotide polymorphism at the position corresponding to position 2,146 in SEQ ID NO:7.

According to a further embodiment the present invention provides the tomato plant as described above, wherein the genome of the plant is characterized by the presence of at least one allele comprising the at least one molecular marker and at least one allele lacking the at least one molecular marker.

According to a further embodiment the present invention provides the tomato plant as described above, wherein the plant comprises within its genome at least one allele comprising a polynucleotide segment having the polynucleotide sequence corresponding to the nucleotide sequence as set forth in SEQ ID NO:3 and at least one allele comprising a polynucleotide segment having the polynucleotide sequence corresponding to the nucleotide sequence as set forth in SEQ ID NO:4.

According to a further embodiment the present invention provides the tomato plant as described above, wherein at least one of the molecular marker is in a heterozygous configuration.

According to a further embodiment the present invention provides the tomato plant as described above, wherein the branching inflorescence phenotype is obtainable from a tomato plant selected from a group consisting of Solanum lycopersicum HAG1, grown from seeds deposited with NCIMB Aberdeen AB21 9YA, Scotland, UK on Apr. 11, 2012 under accession number NCIMB 41958; and Solanum lycopersicum 4468, grown from seeds deposited with NCIMB Aberdeen AB21 9YA, Scotland, UK on Apr. 11, 2012 under accession number NCIMB 41957 and from progenies thereof.

According to a further embodiment the present invention provides the tomato plant as described above, wherein the branching inflorescence phenotype obtainable from a tomato plant Solanum lycopersicum HAG1, grown from seeds deposited with NCIMB Aberdeen AB21 9YA, Scotland, UK on Apr. 11, 2012 under accession number NCIMB 41958, co-segregates with at least one molecular marker selected from a group consisting of: a 271 bp deletion having the nucleotide sequence corresponding to the nucleotide sequence as set forth in SEQ ID NO:5, a single nucleotide polymorphism at the position corresponding to position 2197 in SEQ ID NO:6 and a combination of a single nucleotide polymorphism at the position corresponding to position 2,161 in SEQ ID NO:7 and a single nucleotide polymorphism at the position corresponding to position 2,146 in SEQ ID NO:7.

According to a further embodiment the present invention provides the tomato plant as described above, wherein the branching inflorescence phenotype obtainable from Solanum lycopersicum 4468, grown from seeds deposited with NCIMB Aberdeen AB21 9YA, Scotland, UK on Apr. 11, 2012 under accession number NCIMB 41957, co-segregates with at least one molecular marker selected from a group consisting of: a single nucleotide polymorphism at the position corresponding to position 2,313 in SEQ ID NO:7 and a single nucleotide polymorphism at the position corresponding to position 1,589 in SEQ ID NO:7.

According to a further embodiment the present invention provides the tomato plant as described above, wherein the branching inflorescence phenotype is conferred by a branching inflorescence allele.

According to a further embodiment the present invention provides the tomato plant as described above, wherein the plant comprises within its genome a heterozygous configuration of the branching inflorescence allele.

According to a further embodiment the present invention provides the tomato plant as described above, wherein the plant produces mature fruits with average individual brix level of at least about 4 units.

According to a further embodiment the present invention provides the tomato plant as described above, wherein the plant produces mature fruits with average individual weight of at least about 90 gr.

According to a further embodiment the present invention provides the tomato plant as described above, wherein the plant produces mature fruits with average individual weight of between about 90 gr and about 190 gr.

According to a further embodiment the present invention provides the tomato plant as described above, wherein the plant produces mature fruits with average individual weight of between about 120 gr to about 190 gr.

According to a further embodiment the present invention provides the tomato plant as described above, wherein the plant is characterized by an increase of at least one parameter selected from a group consisting of: fruit weight yield per plant, fruit weight yield per cluster, number of fruits per plant, number of flowers per plant, number of flowers per cluster, fruit brix*yield, earliness and any combination thereof, as compared to a tomato line that is used as the normally branched parent line of the tomato plant.

According to a further embodiment the present invention provides the tomato plant as described above, wherein the plant is characterized by a statistically significant increased fruit weight yield per plant of at least about 8% as compared to the yield of a tomato line that is used as the normally branched parent line of the tomato plant.

According to a further embodiment the present invention provides the tomato plant as described above, wherein the plant is characterized by a statistically significant increased fruit weight yield per plant of between about 8% to about 20% as compared to the yield of a tomato line that is used as the normally branched parent line of the tomato plant.

According to a further embodiment the present invention provides the tomato plant as described above, wherein the plant is characterized by a statistically significant increased fruit weight yield per plant of at least about 18% as compared to the yield of a tomato plant that is used as the normally branched parent line of the tomato plant.

According to a further embodiment the present invention provides the tomato plant as described above, wherein the plant is characterized by an increased average fruit weight yield per cluster of at least about 10% as compared to the yield per cluster of a tomato plant that is used as the normally branched parent line of the tomato plant.

According to a further embodiment the present invention provides the tomato plant as described above, wherein the plant is characterized by an increased average fruit weight yield per cluster of between about 12% and about 25% as compared to the yield per cluster of a tomato plant that is used as the normally branched parent line of the tomato plant.

According to a further embodiment the present invention provides the tomato plant as described above, wherein the plant is characterized by an increased average fruit weight yield per cluster of at least about 24% as compared to the yield per cluster of a tomato plant that is used as the normally branched parent line of the tomato plant.

According to a further embodiment the present invention provides the tomato plant as described above, wherein the plant is characterized by an increased average flower number per cluster of at least about 20% as compared to the average flower number per cluster of a tomato line that is used as the normally branched parent line of the tomato plant.

According to a further embodiment the present invention provides the tomato plant as described above, wherein the plant is characterized by an increased average flower number per cluster of between about 20% to about 80% as compared to the average flower number per cluster of a tomato line that is used as the normally branched parent line of the tomato plant.

According to a further embodiment the present invention provides the tomato plant as described above, wherein the plant is characterized by an increased average flower number per cluster of at least about 60% as compared to the average flower number per cluster of a tomato line that is used as the normally branched parent line of the tomato plant.

According to a further embodiment the present invention provides the tomato plant as described above, wherein the plant is characterized by having an average number of at least about 20 fruits per plant.

According to a further embodiment the present invention provides the tomato plant as described above, wherein the plant displays enhanced earliness parameters as compared to a tomato line that is used as the normally branched parent line of the tomato plant.

According to a further embodiment the present invention provides the tomato plant as described above, wherein the plant is characterized by a decrease of at least about 15% in the average number of days to first ripen fruit as compared to a tomato line that is used as the normally branched parent line of the tomato plant.

According to a further embodiment the present invention provides the tomato plant as described above, wherein the plant is characterized by a decrease of between about 20% and about 50% in the average number of days to first ripen fruit as compared to a tomato line that is used as the normally branched parent line of the tomato plant.

According to a further embodiment the present invention provides the tomato plant as described above, wherein the plant is characterized by a decrease of between about 22% and about 35% in the average number of days to first ripen fruit as compared to a tomato line that is used as the normally branched parent line of the tomato plant.

According to a further embodiment the present invention provides the tomato plant as described above, wherein the normally branched parent line is selected from the group consisting of a Beef type, a Loose type and a Cluster type tomato line.

According to a further embodiment the present invention provides a tomato plant exhibiting a branching inflorescence phenotype, wherein the branching inflorescence phenotype co-segregates with a molecular marker combination selected from the group consisting of: a single nucleotide polymorphism at the position corresponding to position 2,313 in SEQ ID NO:7 combined with a 271 bp indel marker having a nucleotide sequence corresponding to the nucleotide sequence as set forth in SEQ ID NO:5, a single nucleotide polymorphism at the position corresponding to position 1,589 in SEQ ID NO:7 combined with a 271 bp indel marker having a nucleotide sequence corresponding to the nucleotide sequence as set forth in SEQ ID NO:5 and a combination thereof.

According to a further embodiment, the present invention provides the tomato plant as described above, wherein the plant is a hybrid.

According to a further embodiment the present invention provides the pollen of the tomato plant as described above.

According to a further embodiment the present invention provides the ovule of the plant as described above.

According to a further embodiment the present invention provides a tomato fruit derived from the tomato plant as described above.

According to a further embodiment the present invention provides a tomato fruit product derived from the tomato plant as described above.

According to a further embodiment the present invention provides a tomato seed derived from a crossing in which at least one of the parents is a tomato plant as described above.

According to a further embodiment the present invention provides a tomato seed from which the tomato plants as described above originate.

According to a further embodiment the present invention provides plant part of a tomato plant as described above.

According to a further embodiment the present invention provides the seed of the tomato plant as described above, wherein a plant grown from the seed produces a tomato plant exhibiting a branching inflorescence phenotype, wherein the plant produces statistically significant high yield of mature fruits having the characteristics of average individual fruit weight or average individual fruit brix levels or a combination thereof, similar to fruits produced by a tomato line that is used as the normally branched parent line of the tomato plant.

According to a further embodiment the present invention provides the seed as described above, wherein the branching inflorescence phenotype is co-segregating with at least one molecular marker selected from the group consisting of: a 271 bp deletion marker having a nucleotide sequence corresponding to the nucleotide sequence as set forth in SEQ ID NO:5, a single nucleotide polymorphism at the position corresponding to position 2197 in SEQ ID NO:6, a single nucleotide polymorphism at the position corresponding to position 2,313 in SEQ ID NO:7, a single nucleotide polymorphism at the position corresponding to position 1,589 in SEQ ID NO:7 and a combination of a single nucleotide polymorphism at the position corresponding to position 2,161 in SEQ ID NO:7 and a single nucleotide polymorphism at the position corresponding to position 2,146 in SEQ ID NO:7.

According to a further embodiment the present invention provides the seed as described above, wherein at least one of the molecular marker is in a heterozygous configuration.

According to a further embodiment the present invention provides the seed as described above, wherein the branching inflorescence phenotype is obtainable from a tomato plant selected from a group consisting of Solanum lycopersicum HAG1, grown from seeds deposited with NCIMB Aberdeen AB21 9YA, Scotland, UK on Apr. 11, 2012 under accession number NCIMB 41958; and Solanum lycopersicum 4468, grown from seeds deposited with NCIMB Aberdeen AB21 9YA, Scotland, UK on Apr. 11, 2012 under accession number NCIMB 41957 and from progenies thereof.

According to a further embodiment the present invention provides the seed as described above, wherein the plant is characterized by an increase of at least one parameter selected from a group consisting of: fruit weight yield per plant, fruit weight yield per cluster, number of fruits per plant, number of flowers per plant, number of flowers per cluster, fruit brix*yield, earliness and any combination thereof, as compared to a tomato line that is used as the normally branched parent line of the tomato plant.

According to a further embodiment the present invention provides the tomato plant as described above, wherein the plant further comprising within its genome at least one additional trait selected from the group consisting of high germination rate, vigorous growth, herbicide resistance, insect resistance, resistance to bacterial, fungal or viral disease, and resistance to a non-biotic stress, wherein the additional trait is introduced by a method selected from the group consisting of breeding, genetic determinant introgression and transformation.

According to a further embodiment the present invention provides a tissue culture of regenerable cells or protoplasts obtained from the tomato plant as described above or a part thereof.

According to a further embodiment the present invention provides the tissue culture as described above, wherein the regenerable cells or protoplasts are obtainable from a plant part selected from the group consisting of leaves, pollen, embryos, immature embryos, roots, root tips, anthers, meristematic cells, microspores, flowers, cotyledons, pistil, fruit, seeds, seed coat or any combination thereof.

According to a further embodiment the present invention provides the tissue culture as described above, wherein the regenerable cells comprise cells or protoplasts or callus.

According to a further embodiment the present invention provides the tissue culture as described above, wherein the tissue culture regenerates plants having a branching inflorescence phenotype, wherein the plant produces statistically significant high yield of mature fruits having the characteristics of average individual fruit weight or average individual fruit brix levels or a combination thereof, similar to fruits produced by a tomato line that is used as the normally branched parent line of the tomato plant.

According to a further embodiment the present invention provides a cell derived from a tissue culture as described above.

According to a further embodiment the present invention provides a tomato plant regenerated from the tissue culture as described above.

According to a further embodiment the present invention provides a tomato plant exhibiting a branching inflorescence phenotype, wherein the plant produces statistically significant high yield of mature fruits having the characteristics of average individual fruit weight or average individual fruit brix levels or a combination thereof, similar to fruits produced by a tomato line that is used as the normally branched parent line of the tomato plant, further wherein the branching inflorescence phenotype co-segregates with at least one molecular marker selected from a group consisting of: a 271 bp deletion having the nucleotide sequence corresponding to the nucleotide sequence as set forth in SEQ ID NO:5, a single nucleotide polymorphism at the position corresponding to position 2197 in SEQ ID NO:6 and a combination of a single nucleotide polymorphism at the position corresponding to position 2,161 in SEQ ID NO:7 and a single nucleotide polymorphism at the position corresponding to position 2,146 in SEQ ID NO:7.

According to a further embodiment the present invention provides the tomato plant as described above, wherein the fruit yield produced by the plant is similar or higher than the fruit yield produced by a tomato plant having a branching inflorescence phenotype co-segregating with at least one molecular marker selected from a group consisting of: a single nucleotide polymorphism at the position corresponding to position 2,313 in SEQ ID NO:7 and a single nucleotide polymorphism at the position corresponding to position 1,589 in SEQ ID NO:7.

According to a further embodiment the present invention provides a tomato plant exhibiting a branching inflorescence phenotype, wherein the plant produces statistically significant high yield of mature fruits having the characteristics of average individual fruit weight or average individual fruit Brix levels or a combination thereof, similar to fruits produced by a tomato line that is used as the normally branched parent line of the tomato plant, further wherein the branching inflorescence phenotype co-segregates with at least one molecular marker selected from a group consisting of: a single nucleotide polymorphism at the position corresponding to position 2,313 in SEQ ID NO:7 and a single nucleotide polymorphism at the position corresponding to position 1,589 in SEQ ID NO:7.

According to a further embodiment the present invention provides the tomato plant as described above, wherein the fruit yield produced by the plant is similar or higher than the fruit yield produced by a tomato plant having a branching inflorescence phenotype co-segregating with at least one molecular marker selected from a group consisting of: a 271 bp deletion having the nucleotide sequence corresponding to the nucleotide sequence as set forth in SEQ ID NO:5, a single nucleotide polymorphism at the position corresponding to position 2197 in SEQ ID NO:6 and a combination of a single nucleotide polymorphism at the position corresponding to position 2,161 in SEQ ID NO:7 and a single nucleotide polymorphism at the position corresponding to position 2,146 in SEQ ID NO:7.

According to a further embodiment the present invention provides a tomato field or tomato greenhouse comprising tomatoes as described above.

Methods for Producing and Identifying the Tomato Plants Having the Unique Statistically Significant High Yield Properties Plant breeding and hybrid development are an expensive, labour, and time-consuming process. Pedigree breeding and recurrent selection breeding methods are used to develop inbred lines from breeding populations. Breeding programs combine the genetic backgrounds from two or more inbred lines or various other germplasm sources into breeding pools from which new inbred lines are developed by selfing and selection of desired phenotypes and characteristics. The new inbred plants are crossed with other inbred lines and the hybrids from these crosses are evaluated to determine which of those have commercial potential.

As herein disclosed, pedigree breeding may start with the crossing of two genotypes, each of which may have one or more commercially desirable characteristics, that is lacking in the other or which complements the other.

In a preferred embodiment, a tomato plant having a branching or highly branching inflorescence phenotype is crossed with a normally or regularly branched tomato plant, i.e. 4131 or 4466 lines. If the two original parents do not provide all the desired characteristics, other sources can be included in the breeding population in order to generate an established breeding population. In such a pedigree, plants are selfed and selected in successive generations. The hybrid progeny of the first generation is designated F1. Preferred F1 hybrids are, for example, more vigorous than their inbred parents. This hybrid performance (hybrid vigor or heterosis), can be manifested in many polygenic traits, including increased vegetative growth and increased yield.

The introgression of a trait into an elite or commercial or breeding line can be achieved by recurrent selection breeding, for example by backcrossing. In this case, the elite line (recurrent parent) is first crossed to a donor or source line (i.e. the non-recurrent parent) that carries the trait, particularly the "branching inflorescence" trait, for example HAG1 or 4468 lines.

The progeny of such a cross is then mated back to the recurrent parent or to a tomato plant with a distinct genetic background having a normal or regular inflorescence phenotype (as used herein early generation test cross or "EGTC"), followed by selection for the trait in the resultant progeny. The selection may be performed using genetic markers that are herein shown to co-segregate with the branching inflorescence trait. After three, preferably four, more preferably five or more generations of backcrosses with the recurrent parent with selection for the trait, particularly the "branching inflorescence" trait, the progeny is heterozygous for the locus harboring the aforementioned trait, but is like the recurrent parent for most or almost all other genes. Selection for the trait is carried out after each cross using phenotypic evaluation and molecular marker analysis as described in the examples of the present invention.

Marker assisted selection can be performed using one or more of the herein described molecular markers to identify those hybrid plants that contain one or more of the alleles associated with a branching inflorescence phenotype. Alternatively, marker assisted selection can be used to confirm the results obtained from the fruit yield phenotyping analysis.

The tomato plants having statistically significant high yield properties as described herein may be produced by introgression between a highly branched or branched tomato plant as a donor of a branching inflorescence trait and any tomato plant or line having a normal or regular branched phenotype used as a recipient of the branching inflorescence introgression. The selection of the plants having statistically significant high yield properties is carried out using the novel molecular markers and molecular marker combinations disclosed herein that are shown to co-segregate with a branching inflorescence trait.

Thus according to one embodiment, the present invention provides means and methods to identify, screen and produce a tomato plant having a branching inflorescence phenotype, wherein the plant produces statistically significant high yield of mature fruits with average individual fruit weight and/or fruit brix levels similar to fruits produced by a tomato line that is used as the normally branched parent line of the tomato plant.

According to a further embodiment, the present invention provides a method for producing a tomato plant exhibiting a branching inflorescence phenotype, wherein the plant produces statistically significant high yield of mature fruits having the characteristics of average individual fruit weight or average individual fruit brix levels or a combination thereof, similar to fruits produced by a tomato line that is used as the normally branched parent line of the tomato plant. The aforementioned method comprising the steps of: (a) selecting a first tomato plant having a highly branching inflorescence phenotype or a branching inflorescence phenotype and a second tomato plant used as a normally branched parent line; (b) crossing the first and the second tomato plants of step (a) to produce an F1 tomato plant progeny; and (c) evaluating fruit yield parameters of the progeny, and selecting at least one plant producing statistically significant high yield of mature fruits having the characteristics of average individual fruit weight or average individual fruit brix levels or a combination thereof, similar to fruits produced by a tomato line that is used as the normally branched parent line of the tomato plant.

According a further embodiment, the method as defined above comprising additional steps of: (a) analyzing a DNA sample obtained from the progeny of step (b) for the presence of at least one molecular marker selected from the group consisting of: a 271 bp deletion marker having a nucleotide sequence corresponding to the nucleotide sequence as set forth in SEQ ID NO:5, a single nucleotide polymorphism at the position corresponding to position 2197 in SEQ ID NO:6, a single nucleotide polymorphism at the position corresponding to position 2,313 in SEQ ID NO:7, a single nucleotide polymorphism at the position corresponding to position 1,589 in SEQ ID NO:7 and a combination of a single nucleotide polymorphism at the position corresponding to position 2,161 in SEQ ID NO:7 and a single nucleotide polymorphism at the position corresponding to position 2,146 in SEQ ID NO:7, the at least one molecular marker is co-segregating with the branching inflorescence phenotype; and (b) selecting at least one plant having the characteristics of step (a).

According to a further embodiment, the present invention provides a method for producing a tomato plant exhibiting a branching inflorescence phenotype, wherein the plant produces statistically significant high yield of mature fruits having the characteristics of average individual fruit weight or average individual fruit brix levels or a combination thereof, similar to fruits produced by a tomato line that is used as the normally branched parent line of the tomato plant. The aforementioned method comprising the steps of: (a) selecting a first tomato plant having a highly branching inflorescence phenotype or a branching inflorescence phenotype and a second tomato plant used as a normally branched parent line; (b) crossing the first and the second tomato plants of step (a) to produce an F1 tomato plant progeny; (c) analyzing the DNA obtained from the progeny of step (b) for the presence of at least one molecular marker selected from the group consisting of: a 271 bp deletion marker having a nucleotide sequence corresponding to the nucleotide sequence as set forth in SEQ ID NO:5, a single nucleotide polymorphism at the position corresponding to position 2197 in SEQ ID NO:6, a single nucleotide polymorphism at the position corresponding to position 2,313 in SEQ ID NO:7, a single nucleotide polymorphism at the position corresponding to position 1,589 in SEQ ID NO:7 and a combination of a single nucleotide polymorphism at the position corresponding to position 2,161 in SEQ ID NO:7 and a single nucleotide polymorphism at the position corresponding to position 2,146 in SEQ ID NO:7, the at least one molecular marker is co-segregating with the branching inflorescence phenotype; (d) selecting at least one plant having the characteristics of step (c); and, (e) evaluating fruit yield parameters of the at least one selected plant of step (d), and selecting at least one plant producing statistically significant high yield of mature fruits having the characteristics of average individual fruit weight or average individual fruit brix levels or a combination thereof, similar to fruits produced by a tomato line that is used as the normally branched parent line of the tomato plant.

According a further embodiment, the method as defined above comprising an additional step of selecting the parameter from a group consisting of: fruit weight yield per plant, fruit weight yield per cluster, number of fruits per plant, number of flowers per plant, number of flowers per cluster, average fruit weight, average fruit brix, fruit brix*yield, earliness and any combination thereof.

According to a further embodiment, the method as defined above comprising an additional step of selfing the F1 tomato plants to produce F2 tomato plant progeny.

According to a further embodiment, the method as defined above comprising an additional step of selfing at least once the F2 progeny to produce F3 plants and further selecting at least one tomato plant exhibiting a branching inflorescence phenotype, wherein the plant produces statistically significant high yield of mature fruits having the characteristics of average individual fruit weight or average individual fruit brix levels or a combination thereof, similar to fruits produced by a tomato line that is used as the normally branched parent line of the tomato plant.

According to a further embodiment, the method as defined above comprising an additional step of backcrossing at least once the F1 and/or the F2 plants with at least one normally branched parental line, or elite line or breeding tomato line, and selecting at least one tomato plant exhibiting a branching inflorescence phenotype, wherein the plant produces statistically significant high yield of mature fruits having the characteristics of average individual fruit weight or average individual fruit brix levels or a combination thereof, similar to fruits produced by a tomato line that is used as the normally branched parent line of the tomato plant.

According to specific embodiments, the method as defined above comprising an additional step of introducing into the genome of the plant at least one trait selected from the group consisting of: high germination rate, vigorous growth, herbicide resistance, insect resistance, resistance to bacterial, fungal or viral disease, resistance to non biotic stress and any combination thereof.

According to a further embodiment, the method as defined above comprising an additional step of repeating the step of crossing and the step of selecting at least once.

The present invention further provides a tomato plant and parts thereof produced by the method as defined above.

The present invention further provides a method for screening for a tomato plant exhibiting a branching inflorescence phenotype comprising the steps of: screening the genome of the plant for the presence of a molecular marker combination selected from the group consisting of: a single nucleotide polymorphism at the position corresponding to position 2,313 in SEQ ID NO:7 combined with a 271 bp indel marker having a nucleotide sequence corresponding to the nucleotide sequence as set forth in SEQ ID NO:5, and a single nucleotide polymorphism at the position corresponding to position 1,589 in SEQ ID NO:7 combined with a 271 bp indel marker having a nucleotide sequence corresponding to the nucleotide sequence as set forth in SEQ ID NO:5; and a combination thereof; the molecular marker combination co-segregates with a branching inflorescence phenotype; wherein the presence of at least one molecular marker combination selected from a group consisting of: (a) T or A at the position corresponding to position 2,313 of SEQ ID NO:7 combined with a deletion of a 271 bp indel marker having a nucleotide sequence corresponding to the nucleotide sequence as set forth in SEQ ID NO:5, and (b) C or G at the position corresponding to position 2,313 of SEQ ID NO:7 combined with the presence of a 271 bp indel marker having a nucleotide sequence corresponding to the nucleotide sequence as set forth in SEQ ID NO:5, (c) T or A at the position corresponding to position 1,589 of SEQ ID NO:7 combined with a deletion of a 271 bp indel marker having a nucleotide sequence corresponding to the nucleotide sequence as set forth in SEQ ID NO:5, and (d) T or A at the position corresponding to position 1,589 of SEQ ID NO:7 combined with the presence of a 271 bp indel marker having a nucleotide sequence corresponding to the nucleotide sequence as set forth in SEQ ID NO:5; is indicative of a plant having a branching inflorescence phenotype.

The present invention further provides a method for identifying haplotypes associated with a branching inflorescence phenotype, the method comprising the steps of: (a) isolating a DNA sample from a tomato plant; (b) analyzing the DNA for the presence of at least one molecular marker combination selected from the group consisting of: (i) a single nucleotide polymorphism at the position corresponding to position 2,313 in SEQ ID NO:7 combined with a 271 bp indel marker having a nucleotide sequence corresponding to the nucleotide sequence as set forth in SEQ ID NO:5, and (ii) a single nucleotide polymorphism at the position corresponding to position 1,589 in SEQ ID NO:7 combined with a 271 bp deletion marker having a nucleotide sequence corresponding to the nucleotide sequence as set forth in SEQ ID NO:5;

wherein the presence of at least one molecular marker combination selected from a group consisting of: (a) T or A at the position corresponding to position 2,313 of SEQ ID NO:7 combined with a deletion of a 271 bp indel marker having a nucleotide sequence corresponding to the nucleotide sequence as set forth in SEQ ID NO:5, (b) C or G at the position corresponding to position 2,313 of SEQ ID NO:7 combined with the presence of a 271 bp indel marker having a nucleotide sequence corresponding to the nucleotide sequence as set forth in SEQ ID NO:5, (c) T or A at the position corresponding to position 1,589 of SEQ ID NO:7 combined with a deletion of a 271 bp indel marker having a nucleotide sequence corresponding to the nucleotide sequence as set forth in SEQ ID NO:5, and (d) T or A at the position corresponding to position 1,589 of SEQ ID NO:7 combined with the presence of a 271 bp indel marker having a nucleotide sequence corresponding to the nucleotide sequence as set forth in SEQ ID NO:5; is indicative of a plant having a branching inflorescence phenotype;

wherein the at least one molecular marker combination co-segregates with a branching inflorescence phenotype, further wherein the analysis is configured to discriminate between normally branching inflorescence phenotype and branching inflorescence phenotypes having distinct haplotype.

According to a further embodiment, the method as defined above wherein the plant comprising within its genome at least one molecular marker combination selected from the group consisting of: (a) T or A at the position corresponding to position 2,313 of SEQ ID NO:7 combined with a deletion of a 271 bp indel marker having a nucleotide sequence corresponding to the nucleotide sequence as set forth in SEQ ID NO:5, and (b) T or A at the position corresponding to position 1,589 of SEQ ID NO:7 combined with a deletion of a 271 bp indel marker having a nucleotide sequence corresponding to the nucleotide sequence as set forth in SEQ ID NO:5, is obtainable from a tomato plant *Solanum lycopersicum* HAG1, grown from seeds deposited with NCIMB Aberdeen AB21 9YA, Scotland, UK on Apr. 11, 2012 under accession number NCIMB 41958 and from progenies thereof.

According to a further embodiment, the method as defined above wherein the plant comprising within its genome at least one molecular marker combination selected from the group consisting of (a) C or G at the position corresponding to position 2,313 of SEQ ID NO:7 combined with the presence of a 271 bp indel marker having a nucleotide sequence corresponding to the nucleotide sequence as set forth in SEQ ID NO:5, (b) T or A at the position corresponding to position 1,589 of SEQ ID NO:7 combined with the presence of a 271 bp indel marker having a nucleotide sequence corresponding to the nucleotide sequence as set forth in SEQ ID NO:5 is obtainable from *Solanum lycopersicum* 4468, grown from seeds deposited with NCIMB Aberdeen AB21 9YA, Scotland, UK on Apr. 11, 2012 under accession number NCIMB 41957 and from progenies thereof.

According to a further aspect, the present invention provides a method for detecting a tomato plant exhibiting a branching inflorescence phenotype, wherein the plant produces statistically significant high yield of mature fruits having the characteristics of average individual fruit weight or average individual fruit brix levels or a combination thereof, similar to fruits produced by a tomato line that is used as the normally branched parent line of the tomato plant, the method comprising the steps of: (a) isolating a genomic DNA sample form the plant; (b) analyzing the DNA for the presence of at least one molecular marker selected from the group consisting of: a 271 bp deletion marker having a nucleotide sequence corresponding to the nucleotide sequence as set forth in SEQ ID NO:5, a single nucleotide polymorphism at the position corresponding to position 2197 in SEQ ID NO:6, a single nucleotide polymorphism at the position corresponding to position 2,313 in SEQ ID NO:7, a single nucleotide polymorphism at the position corresponding to position 1,589 in SEQ ID NO:7 and a combination of a single nucleotide polymorphism at the position corresponding to position 2,161 in SEQ ID NO:7 and a single nucleotide polymorphism at the position corresponding to position 2,146 in SEQ ID NO:7, the at least one molecular marker is co-segregating with a branching inflorescence phenotype; (c) selecting at least one plant having the characteristics of step (b); and, (d) evaluating fruit yield parameters of the at least one selected plant of step (c), and selecting at least one plant producing statistically significant high yield of mature fruits having the characteristics of average individual fruit weight or average individual fruit brix levels or a combination thereof, similar to fruits produced by a tomato line that is used as the normally branched parent line of the tomato plant.

According to a further aspect, the method as defined above further comprising additional steps of: (a) amplifying a DNA segment using a first primer having a polynucleotide sequence as set forth in SEQ ID NO:1 and a second primer having a polynucleotide sequence as set forth in SEQ ID NO:2; and, (b) analyzing the amplified DNA segments produced by the amplification of step (a), wherein the presence of a DNA segment having a polynucleotide sequence corresponding to the sequence as set forth in SEQ ID NO:3 and a DNA segment having a polynucleotide sequence corresponding to the sequence as set forth in SEQ ID NO:4, is indicative of a plant having a branching inflorescence phenotype, wherein the plant produces statistically significant high yield of mature fruits having the characteristics of average individual fruit weight or average individual fruit brix levels or a combination thereof, similar to fruits produced by a tomato line that is used as the normally branched parent line of the tomato plant.

According to a further aspect, the present invention provides an oligonucleotide primer pair having the sequence as set forth in SEQ ID NO:1 and SEQ ID NO:2, wherein the sequences are suitable for the detection of a tomato plant exhibiting a branching inflorescence phenotype, wherein the plant produces statistically significant high yield of mature fruits having the characteristics of average individual fruit weight or average individual fruit brix levels or a combination thereof, similar to fruits produced by a tomato line that is used as the normally branched parent line of the tomato plant.

According to a further aspect, the present invention provides an isolated nucleotide sequence having at least 90% sequence identity with the sequence selected from a group consisting of at least one of the nucleotide sequences corresponding to the nucleotide sequences as set forth in: SEQ ID NO:3, SEQ ID NO:4 and SEQ ID NO:5 and any combination thereof, wherein the sequences are suitable for the detection of a tomato plant exhibiting a branching inflorescence phenotype, wherein the plant produces statistically significant high yield of mature fruits having the characteristics of average individual fruit weight or average individual fruit brix levels or a combination thereof, similar to fruits produced by a tomato line that is used as the normally branched parent line of the tomato plant.

According to a further aspect of the invention, a use of a single nucleotide polymorphism or a polynucleotide sequence selected from a group consisting of: a 271 bp deletion marker having a nucleotide sequence corresponding to the nucleotide sequence as set forth in SEQ ID NO:5, a single nucleotide polymorphism at the position corresponding to position 2197 in SEQ ID NO:6, a single nucleotide polymorphism at the position corresponding to position 2,313 in SEQ ID NO:7, a single nucleotide polymorphism at the position corresponding to position 1,589 in SEQ ID NO:7 and a combination of a single nucleotide polymorphism at the position corresponding to position 2,161 in SEQ ID NO:7 and a single nucleotide polymorphism at the position corresponding to position 2,146 in SEQ ID NO:7 and any combination thereof, in marker based selection of a tomato plant exhibiting a branching inflorescence phenotype, wherein the plant produces statistically significant high yield of mature fruits having the characteristics of average individual fruit weight or average individual fruit Brix levels or a combination thereof, similar to fruits produced by a tomato line that is used as the normally branched parent line of the tomato plant.

According to a further aspect of the invention, a use of a single nucleotide polymorphism or polynucleotide sequence selected from a group consisting of: (a) a single nucleotide polymorphism at the position corresponding to position 2,313 in SEQ ID NO:7 combined with a 271 bp indel marker having a nucleotide sequence corresponding to the nucleotide sequence as set forth in SEQ ID NO:5, and (b) a single nucleotide polymorphism at the position corresponding to position 1,589 in SEQ ID NO:7 combined with a 271 bp indel marker having a nucleotide sequence corresponding to the nucleotide sequence as set forth in SEQ ID NO:5; in marker based selection of a tomato plant having a branching inflorescence phenotype.

The following examples are presented in order to more fully illustrate certain embodiments of the invention. They should in no way, however, be construed as limiting the broad scope of the invention. One skilled in the art can readily devise many variations and modifications of the principles disclosed herein without departing from the spirit and scope of the invention.

EXAMPLES

Example 1

Production of Tomato Plants with Unique High Yield Properties

A source material used for the production of the statistically significant high yield tomato plants of the present invention may include tomato lines and/or accessions with a highly branched inflorescence (i.e. having an average of 50-100 flowers per inflorescence) or a branching inflorescence phenotype (i.e. having an average of at least 10 flowers per inflorescence). An exemplary source material could be tomato line HAG1, seeds of which have been deposited on 11 Apr. 2012, under deposit number NCIMB 41958 according to the Budapest treaty. Alternative exemplary source material could be tomato line 4468, seeds of which have been deposited on 11 Apr. 2012, under deposit number NCIMB 41957 according to the Budapest treaty. Such highly branched or branched inflorescence tomato plant sources or donors could be crossed with any tomato line or tomato plant having a regular or normally branched inflorescence phenotype. Normally branched inflorescence plants may include, for example, germplasm tomato lines, breeding lines, advanced breeding lines, elite lines and cultivated or commercial tomato lines. Thus, it is emphasized that a crossing scheme as described herein is one example among many others, of a possible breeding scheme or pedigree that could be used to produce the statistically significant high yield tomato plants of the present invention identified by the molecular markers as disclosed herein.

Reference is now made to FIG. 1 showing an exemplary breeding scheme that could be used to produce the tomato plants of the present invention. As presented in this figure, a highly branching inflorescence line (i.e. HAG1 or 4468) is crossed with a normally branched inflorescence line (i.e. 4131 commercial line) to produce F1 generation plants. Selected F1 plants were selfed to produce F2 generation plants. Selected F2 plants, screened for the genetic markers as described inter alia and having the claimed characteristics of significantly high yield of mature fruits were then backcrossed with the normally branched inflorescences parental line (i.e. 4131) to produce BC1 4131 population. The phenotypic characteristics of significantly high yield of mature fruits with average individual fruit weight and/or fruit brix levels similar to fruits produced by a tomato line that is used as the normally branched parent line of said tomato plant were tested in at least three genetic backgrounds:
 (a) In beef type tomato plants having average individual fruit weight of 300 to 400 gr, by selfing BC1 4131 selected plants (BC1F2-4131);
 (b) In loose type tomato plants having average individual fruit weight of 200 to 300 gr, by crossing BC1 4131 selected plants with line 64 (F1-64);
 (c) In cluster type tomato plants having average individual fruit weight of 100 to 200 gr, by crossing BC1 4131 selected plants with line 60 (F1-60);
The plants of the above populations were subjected to phenotypic and molecular analysis.

Reference is now made to FIG. 2, showing a further representative breeding scheme that could be used to produce the tomato plants of the present invention. In this embodiment, tomato line HAG1 has been crossed with tomato line 4131 to produce F1 population. F1 plants were grown, and the seeds were self pollinated to produce F2 generation plants. About 70 F2 plants were planted at Hazahv. The plants were subjected to flower and fruit phenotypic observations at the Autumn-Winter season (designated season_1 in FIG. 2). This screening procedure revealed the presence of plants having a branching inflorescence phenotype characterized by increased number of fruits per plant relative to the parental line 4131, but surprisingly without the expense of individual fruit weight that unexpectedly was similar to the parental line 4131. In other words, the increased amount of fruits produced by the F2 plants did not affect individual fruit weight and thus the fruit weight yield produced by the plants was elevated. These statistically significant high yield tomato plants were genetically analyzed for the presence of unique DNA molecular markers segregating with the branching inflorescence trait as detailed below.

Based on these screening processes, selected F2 plants were selfed to produce F3 population. In addition four F2 plants were selected (designated F2s1, F2s2 and F2s3 and F2s4 in FIG. 2) for backcrossing. Each of the selected F2 plants was backcrossed with the 4131 line that is used as the normally branched parent line of said tomato plant, to produce BC1 populations. Those BC1 plants were planted at Hazahv, Israel in a plant stand estimated at about 2500 plants per dunam. About 20 to 30 progeny plants derived of each cross were grown in separate plots numbered 1 to 4 (designated plot1 to plot4 in FIG. 2). The BC1 plants of each plot were subjected to yield evaluation at the spring-summer growing season (designated season_2 in FIG. 2). The yield evaluation included flower number analysis and fruit number and weight/size analysis. The plants were further subjected to molecular marker examination as herein described.

These screening processes resulted in the selection of three plants designated BC1s1, BC1s2 and BC1s3 (see FIG. 2) characterized by having elevated flower number and fruit number, and in addition producing the largest fruits. The aforementioned selected plants included two plants originated from plot1 (designated BC1s1 and BC1s2 in FIG. 2) and one plant derived of plot2 (designated BCs3 in FIG. 2). Each of the three BC1 selected progeny was subjected to the following crosses: (1) self pollination to produce BC1F2 population (designated BC1F2-1, BC1F2-2 and BC1F2-3 in FIG. 2); (2) backcrossing with 4131 parental line to produce BC2 population (designated BC2-1, BC2-2 and BC2-3 in FIG. 2); and, (3) Early Generation Test Cross (EGTC), which is herein defined as a cross between at least one BC1 plant and a tomato line having a genetic background which is distinct from the genetic background of the parental line. An example of an EGTC, among many other possibilities that could be used in the crossing pedigree of the present invention could be between BC1 generation plants, and Hazera's breeding line 60. The progeny populations of these crosses are designated EGTC-60-1, EGTC-60-2 and EGTC-60-3 in FIG. 2; and, (4) a further example could be EGTC with Hazera's tomato breeding line 64. The progeny populations of these crosses are designated EGTC-64-1, EGTC-64-2 and EGTC-64-3 in FIG. 2.

A further exemplary source of a branching inflorescence trait could be tomato line 4468 of the Roma type, seeds of which have been deposited on 11 Apr. 2012 under deposit number NCIMB 41957 according to the Budapest treaty.

TABLE 1

| | | |
|---|---|---|
| Breeding significantly high yield tomato plants using 4468 branching inflorescence source | | |
| Hybrid | P1- branching inflorescence line | P2- normally branched inflorescence line |
| Heterozygote 3291 | Homozygote to branching allele 4468 | Homozygote to non-branching allele 4466 |

As shown in Table 1, further embodiments of the invention included crossing of 4468 line having branched inflorescence phenotype with a normally branched 4466 tomato line to produce F1 plants. Exemplary F1 plant screened for the claimed high yield characteristics can be hybrid line 3291. Three genotypes were examined in parallel including the two parental lines as control, and the hybrid line. The plants were phenotyped and genotyped. The plants were tested in 8 blocks, each block containing the three genotypes, 4-5 plants of each genotype.

The aforementioned donor lines of the branching inflorescence trait could be introgressed with any regularly or normally branched tomato plant. F1 population was produced. F1 plants were grown, and the seeds were self pollinated to produce F2 generation plants. Candidates of the F2 population were planted and grown in blocks and the grown plants were subjected to phenotyping according to, but not limited to, flower number, fruit number, fruit weight, fruit brix, brix*yield or any combination thereof. Fruit collection was done on all the clusters (i.e. 1-9). Dates of flowering and ripening were also measured.

Example 2

Genetic Sources and Progeny Populations Exemplified in the Present Invention

Reference is now made to Table 2, showing the sources and genetic backgrounds used as examples of potential parental lines and their hybrid progenies. The populations are herein described mainly with respect to their inflorescence and fruit characteristic features according to definitions used within the UPOV guidelines for Tomato *Lycopersicon lycopersicum* (UPOV TG/44/10 Guidelines for the conduct of tests for Distinctness, Uniformity and Stability).

TABLE 2

| | | | | | |
|---|---|---|---|---|---|
| Lines and progeny populations exemplified in the present invention | | | | | |
| | Plant growth type (section 2 under UPOV guidelines) | Length of internode (between $1^{st}$ and $4^{th}$ inflorescence (section 5 under UPOV guidelines) | inflorescence type of $2^{nd}$ and $3^{rd}$ truss (section 16 under UPOV guidelines) | Fruit: size (section 22 under UPOV guidelines) | Fruit: shape in longitudinal section (section 24 under UPOV guidelines) |
| Line | | | | | |
| HAG1 | indeterminate | long | mainly multiparous (50-100 flowers per inflorescence) | Very small | pear-shaped |
| 4468 | indeterminate | medium | Intermediate (about 10 flowers per inflorescence) | small | elliptic |
| 4131 | indeterminate | medium | uniparous | Very large | slightly flattened |
| 4466 | indeterminate | medium | intermediate (3-5 fruits per inflorescence) | small | elliptic |

TABLE 2-continued

Lines and progeny populations exemplified in the present invention

| | Plant growth type (section 2 under UPOV guidelines) | Length of internode (between 1st and 4th inflorescence (section 5 under UPOV guidelines) | inflorescence type of 2nd and 3rd truss (section 16 under UPOV guidelines) | Fruit: size (section 22 under UPOV guidelines) | Fruit: shape in longitudinal section (section 24 under UPOV guidelines) |
|---|---|---|---|---|---|
| 64 | indeterminate | medium | Intermediate (about 6 flowers per inflorescence | Large | slightly flattened |
| 60 | indeterminate | medium | Intermediate (about 7 flowers per inflorescence | Medium | circular |
| Hybrid progeny population | | | | | |
| BC2 | indeterminate | medium | Intermediate (about 8 flowers per inflorescence | Very large | slightly flattened |
| BC1F2 | indeterminate | medium | Intermediate (about 9 flowers per inflorescence | Very large | |
| EGTC 64 | indeterminate | medium | Intermediate (about 8 flowers per inflorescence | large | slightly flattened |
| EGTC 60 | indeterminate | medium | Intermediate (about 9 flowers per inflorescence | medium | circular |
| 160 | indeterminate | medium | Intermediate (about 10 flowers per inflorescence | small | elliptic |
| 3291 | indeterminate | medium | Intermediate (7 fruits per cluster) | small | elliptic |

The BC1F2, BC2, EGTC-60 and EGTC-64 populations (FIG. 2) were planted at Hazahv. The plants were grown in separate plots, in greenhouse conditions in a plant stand estimated at 2500 plants per dunam.

About 20 progeny plants of each of the BC1F2, BC2, EGTC-60 and EGTC-64 populations (total number of about 250 plants) were genetically and phenotypically analyzed. Detailed fruit measurements were performed at the Autumn-Winter season (designated season_3 in FIG. 2), and included evaluation of yield parameters such as average number of flowers per plant, average number of flowers per cluster, yield of fruit weight per plant, yield of fruit weight per cluster, average individual fruit weight, fruit brix level and fruit earliness parameters.

In further embodiments, F1 plants were produced by the cross between 4468 line, having branched inflorescence phenotype, and a normally branched 4466 tomato line. During the spring season, about 40 F1 plants were tested in 8 blocks, each block containing 5 F1 plants and 5 plants of each inbred parental line (4466 and 4468). In addition, each block contained 15-20 F2 plants from the population that was used to generate the 4468 inbred line. These plants were also genotyped and phenotyped.

Thus, the novel and unique statistically significant high yield phenotypic characteristics of the tomato plants of the present invention, identified by specific genetic markers, were demonstrated throughout the pedigree generations, in distinct growing seasons and in at least three distinct independent tomato genetic backgrounds having different inflorescence and fruit features (see Table 2).

Example 3

Evaluation of Yield Characteristics

Experiment I
Tomato Hybrids Based on Hag1 Branching Inflorescence Phenotype source The plant populations resulted from the pedigrees described in Figures 1 and 2 were evaluated for various phenotypic characteristics, especially yield characteristics including, but not limited to, flower number and fruit number, cluster weight measurements, average fruit weight per plant, average fruit weight per cluster, average individual fruit weight, fruit brix level and fruit earliness. The yield parameters were evaluated at several different genetic backgrounds, examples of which are presented in Table 2, and at the various pedigree generations (see FIG. 2 and Table 2). In each generation or tested population the yield parameters were compared between plants lacking the branching inflorescence trait introgression (−/−) and thus having a regular or normal type inflorescence phenotype (i.e. less than 7 flowers per inflorescence), and plants heterozygous for the branching inflorescence introgression (+/−) and having a branching inflorescence phenotype (i.e. more than 7 flowers per inflorescence). It is noted that the genotype of the plants was evaluated using the herein disclosed novel specific genetic markers and specific genetic marker combinations that co segregate with the branching inflorescence introgression allele.

Evaluation of Fruit Yield Parameters
Reference is now made to Table 3, summarizing the fruit yield evaluation results measured at the Autumn-Winter growing season (designated Season_3 in FIGS. 1 and 2). These yield parameters were analyzed by picking the fruits on 4 independent harvest days. In each harvest, the clusters of each plant having 70% of mature fruits were picked and measured. Fruit yield parameters such as average fruit weight per plant and average fruit weight per cluster were compared between plants lacking the branching inflorescence introgression, having a regular inflorescence phenotype (−/−) and plants heterozygous for the branching inflorescence introgression (+/−), having a branching inflorescence phenotype. The results in Table 3 demonstrate that the average fruit weight per plant is increased by a range of between about 8% and about 18% in the heterozygous branched inflorescence plants (+/−) relative to the regular inflorescence plants lacking the branching inflorescence introgression (−/−). The most significant increase (about 18%) was observed at the BC1 F2 population having the 4131 line genetic background.

Figure 3:
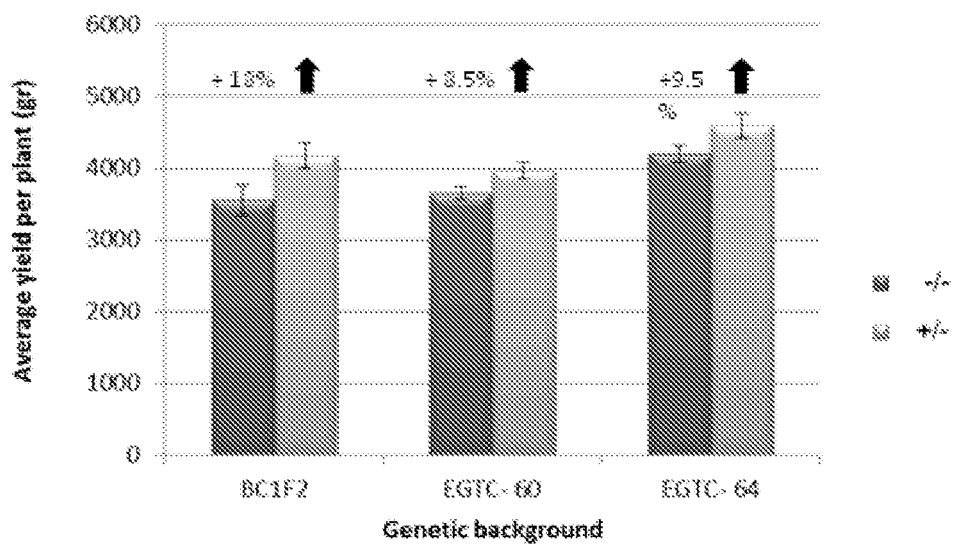
FIG. 3 is illustrating a graphic representation of fruit yield increase in tomato plants of different genetic backgrounds, derived from the crosses as described in FIG. 2.

The fruit yield increase in heterozygous configuration of the branching inflorescence allele is further demonstrated in FIG. 3, graphically showing the heterotic effect on yield, specifically increased yield of between about 8.5% and 18% affected by the genetic background.

It is further shown in Table 3 that the average fruit weight per cluster is elevated by a range of between about 12% to about 24% in the heterozygous branching inflorescence plants (+/−) relative to the plants lacking the branching inflorescence introgression (−/−). It is noted that a highly beneficial increase of more than about 24% in fruit weight per cluster was shown for the 4131 genetic background.

of the measured plants in said plant population and dividing it by the number of plants in the population.

Figure 4:
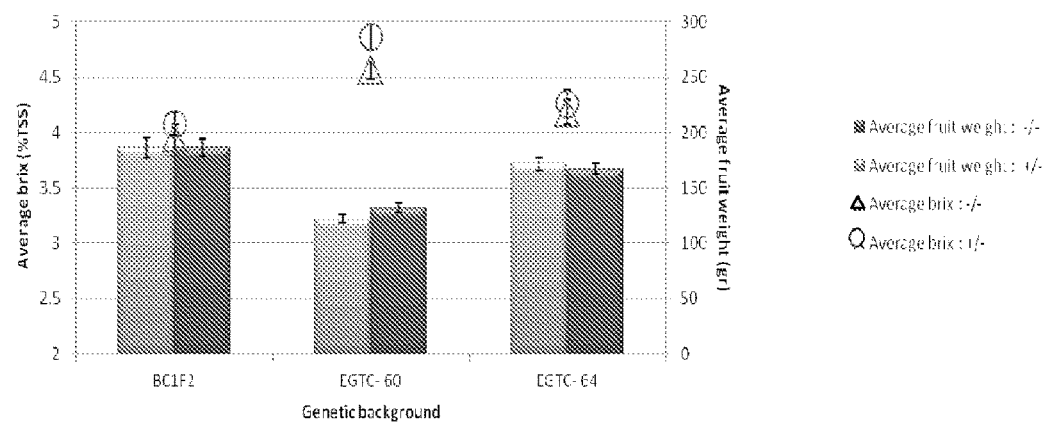
FIG. 4 is illustrating a graphic representation showing the maintenance of individual fruit weight and fruit brix values in different genetic backgrounds, derived from the crosses as described in FIG. 2.

As can be seen in Table 4 and FIG. 4, the average individual fruit weight is surprisingly similar between the plants heterozygous for the branching inflorescence introgression (+/−), having a branching inflorescence phenotype and the plants lacking said introgression (−/−), having a regular inflorescence phenotype. As indicated in Table 4 and FIG. 4, the plants heterozygous for the branching inflorescence introgression (+/−) produce fruits with average individual weight of above about 100 gr in all genetic backgrounds that are selected to be exemplified.

To conclude, the average individual fruit weight was substantially similar between plants heterozygous for the branching inflorescence introgression (+/−) and plants lacking said introgression (−/−) in all the exemplified genetic backgrounds. Thus, although the hybrid plants are characterized by a branching inflorescence phenotype, i.e. comprising more than about 7 flowers per inflorescence, these plants produce fruits with an average individual fruit weight which is substantially similar to tomato plants having the same genetic background but lacking the branching inflorescence introgression. These reference tomato plants are characterized by a regular inflorescence, comprising preferably up to about 6 flowers per inflorescence (Table 2). For example, BC1F2 hybrid plants having the 4131 genetic background produce fruits with average individual fruit

TABLE 3

Yield evaluation results by genetic background

| Genetic background | Population | Average fruit yield/plant (g) | | | | Average fruit yield/cluster (g) | | | |
|---|---|---|---|---|---|---|---|---|---|
| | | −/− | −/+ | Yield/plant increase (%) | Significance level | −/− | −/+ | Yield/cluster increase (%) | Significance level |
| 60 | EGTC | 3657 | 3967 | 8.5 | ** | 570 | 643 | 12.9 | ** |
| 64 | EGTC | 4195 | 4595 | 9.5 | * | 649 | 763 | 17.5 | **** |
| 4131 | BC1F2 | 3533.1 | 4170 | 18.0 | ** | 615.6 | 765 | 24.2 | **** |

*—significance level = 0.1
**—significance level = 0.05
***—significance level = 0.01
****—significance level = 0.001
EGTC—Early Generation Test Cross Thus the results described above show that the tomato plants herein disclosed, have significant commercially valuable properties of increased fruit weight yield in the heterozygote plants. This valuable and unpredictable heterotic effect is demonstrated in different genetic backgrounds, exemplified. The tomato plants having the unique statistically significant high yield properties are identified by specific novel genetic markers provided by the present disclosure.

Reference is now made to Table 4 and FIG. 4, showing that the tomato plants of the present invention posses additional important yield parameters, including large size fruits with enhanced brix features. The values displayed in Table 4 and FIG. 4, represent an average value of 10 independently measured mature fruits of the same plant. The average individual fruit weight and average individual fruit brix values of a certain plant population (i.e. BC1F2, BC2, EGTC-60 or EGTC-64) refers to the mean value as determined by calculating the sum of the average value per plant weight of about 186 g, which is almost identical to the average individual fruit weight of a BC1F2 plant, lacking the branching inflorescence introgression. It is therefore demonstrated that the present invention provides tomato plants having a branching inflorescence phenotype but surprisingly produce increased fruit weight yield with average individual fruit weight, which is similar to the fruits produced by a corresponding elite or breeding line tomato plant lacking the branching inflorescence introgression, and having similar genetic background.

It is further demonstrated in Table 4 and FIG. 4 that the plants heterozygous for the branching inflorescence introgression (+/−) have average fruit brix values, which are similar to the fruit brix values or slightly elevated, of plants lacking said introgression (−/−) and having the same genetic background, as shown for example in the EGTC populations having the genetic background of line 60 and 64 and in BC1F2 population having the 4131 genetic background.

TABLE 4

Average weight per fruit and brix parameters by genetic background

| genetic background | Population | Average individual fruit weight (g) | | | Average individual fruit TSS (%) | | |
|---|---|---|---|---|---|---|---|
| | | −/− | +/− | Significance level | −/− | +/− | significance level |
| 60 | EGTC | 131.3 | 121.8 | n.s. | 4.6 | 4.9 | ** |
| 64 | EGTC | 167.5 | 172.7 | n.s. | 4.1 | 4.2 | n.s. |
| 4131 | BC1F2 | 186.4 | 186.4 | n.s. | 3.9 | 4.0 | n.s. |

**—significance level = 0.05
n.s.—not significant
EGTC—Early Generation Test Cross Thus, it is herein demonstrated that the tomato plants of the present invention are characterized by a branching inflorescence phenotype but surprisingly produce statistically significant high yield of large type mature fruits of individual fruit weight of above about 100 gr. These highly beneficial properties are unexpected as tomato plants having a branching inflorescence phenotype, are known to be associated with deleterious traits such as decreased ability of fruit setting (as compared to the increased number of flowers per plant), decreased fruit size (about 30 gr per fruit) and thus having a reduced fruit weight yield. On the other hand, the tomato plants of the present invention, comprising a branching inflorescence phenotype produce statistically significant increased yield of fruit weight, without damaging individual fruit weight and/or individual fruit brix values.

Flower Number Evaluation

Figure 5A:
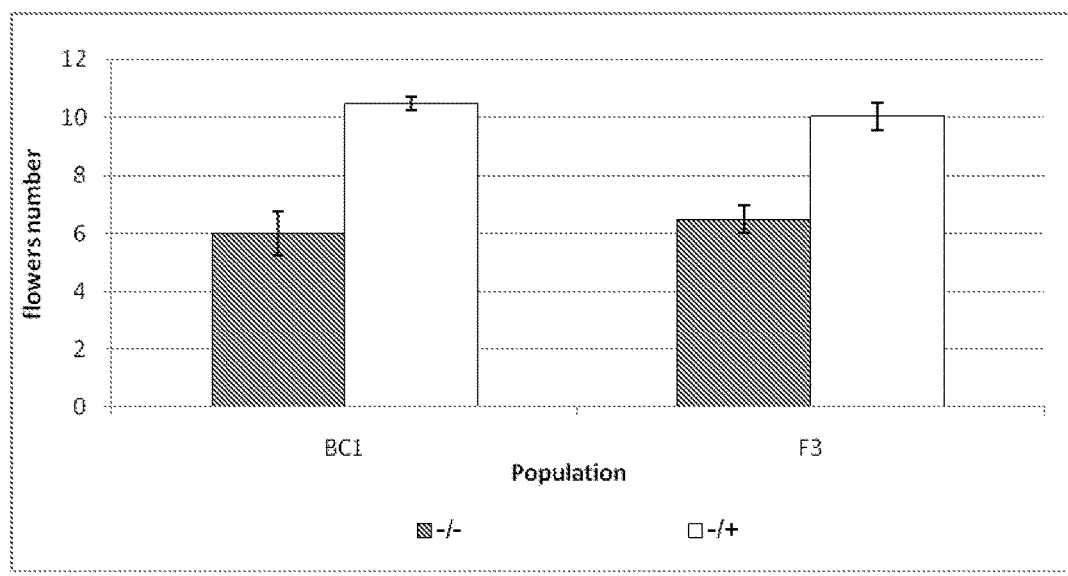
FIG. 5A is illustrating a graphic representation of the number of flowers per cluster by plant population as an embodiment of the present invention.
Figure 5B:
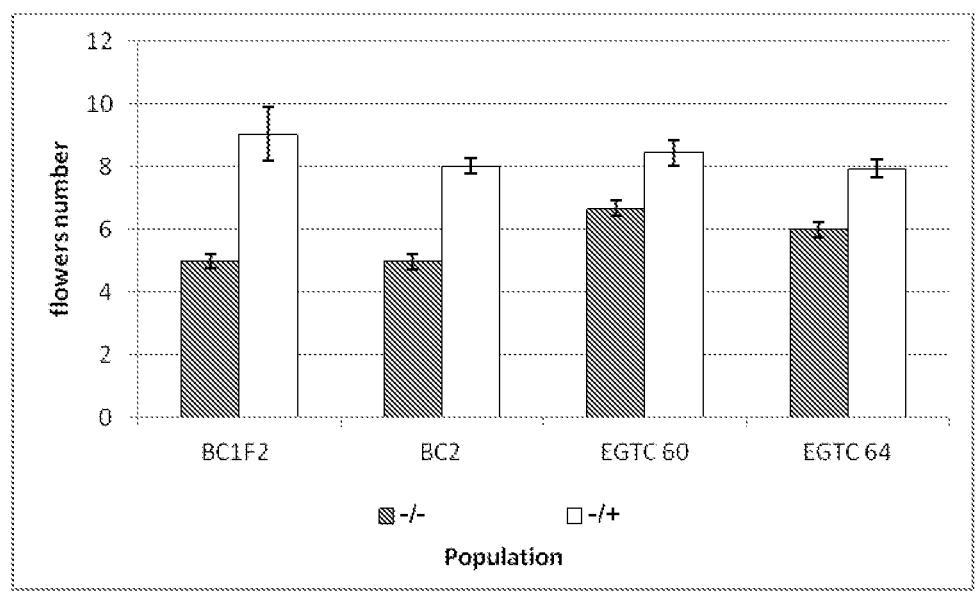
FIG. 5B is illustrating a graphic representation of the number of flowers per cluster by plant population and genetic background as an embodiment of the present invention.

Reference is now made to FIG. 5, graphically summarizing the results describing the average number of flowers per cluster in plants lacking the branching inflorescence introgression (−/−) as compared to plants heterozygous for the branching inflorescence introgression (+/−). FIG. 5A describes the average number of flowers per cluster in F3 and BC1 populations as measured at the Spring-Summer growing season (designated Season_2). FIG. 5B describes the average number of flowers per cluster in BC2, BC1F2, EGTC-60 and EGTC-64 populations and genetic backgrounds as measured at the Autumn-Winter growing season (designated Season_3).

The results described in FIG. 5A and FIG. 5B clearly show that the number of flowers per cluster is significantly increased in the plants heterozygous for the branching inflorescence introgression (+/−) relative to plants lacking said introgression (−/−) in all the tested populations and genetic backgrounds. More specifically the average number of flowers per cluster is demonstrated to be increased by more than about 25% in plants heterozygous for the branching inflorescence introgression (+/−) relative to the plants lacking said introgression (−/−). In fact the average number of flowers per cluster in the heterozygous branched inflorescence type plants (+/−) is increased by an average of about 54% at the F3 population, by an average of about 75% at the BC1 populations (FIG. 5A), by an average of about 32% at the EGTC-64 populations, by an average of about 26% at the EGTC-60 populations, by an average of about 60% at the BC2 populations and at the BC1F2 populations the average number of flowers per cluster is statistically significantly increased by an average of about 80% relative to the regular inflorescence type plants lacking the branching inflorescence introgression.

Reference is now made to Table 5, showing assessment of earliness parameters. As shown in Table 5, plants heterozygous for the branching inflorescence introgression (+/−) presented a significantly shortened ripening period as compared to plants lacking the introgression (−/−), in all genetic backgrounds and plant populations tested. The heterozygous plants having the genetic background of line 4131 demonstrated a highly beneficial decrease of about 34% % at the average number of days to first ripen fruit at cluster 6 (C6).

TABLE 5

Earliness parameters by genetic background

| Genetic background | Population | Average of days to first ripen C6 fruit | | | |
|---|---|---|---|---|---|
| | | −/− | +/− | Earliness increment (%) | Significance level |
| 60 | EGTC | 89.5 | 69.4 | 22.5 | ** |
| 64 | EGTC | 93.4 | 64.6 | 30.8 | ** |
| 4131 | BC1F2 | 64.2 | 42.5 | 33.8 | ** |

** significance = 0.01-0.05
EGTC—Early Generation Test Cross

To conclude, the tomato plants of the present invention having heterozygous configuration of the branching inflorescence trait, which is identified by specific genetic markers as disclosed herewith, are surprisingly characterized by highly valuable agricultural properties of statistically significant increased fruit weight as compared to tomato lines lacking the branching inflorescence trait and having substantially similar genetic background. The increased fruit yield characteristic is unexpectedly combined with the advantage of having a desirable individual fruit weight, fruit brix and/or enhanced earliness characteristics.

It is a main aspect of the invention that the tomato plants having heterozygous configuration of the branching inflorescence trait, produce statistically significant high yield of fruits with desirable agricultural and commercially valuable properties selected from a group comprising increased fruit weight yield per cluster, increased fruit weight yield per plant, individual fruit weight of above 100 gr, fruit brix value of above 4 units, enhanced brix*yield fruit values, enhanced earliness characteristics and combinations thereof, as compared to corresponding tomato lines lacking the branching inflorescence introgression, preferably breeding lines and lines suitable for commercial growth.

Thus it is herein shown that by using a breeding process as exemplified by the present disclosure including the novel genetic markers and selection steps, disclosed in the present invention, statistically significant high fruit yield tomato plants are produced which has increased flower number and fruit weight characteristics without the expense of desirable individual fruit parameters of average weight per fruit, fruit brix level and/or earliness.

Experiment II:
Tomato Hybrids Based on 4468 Branching Inflorescence Phenotype Source Increased fruit yield is a key trait in tomato breeding. One of the possible ways of increasing mature fruit yield is by increasing the number of flowers on each inflorescence, which increases the number of fruits on each truss. The described example shows that the use of the molecular markers disclosed by the present invention enables selection of plants bearing an increased number of fruit on each truss, such selected plants being without diminished fruit size or reduced total soluble solids. To this end, hybrid plants created by crossing a line harboring the specific indel or SNP or combination thereof with tomato lines that do not contain the specific indel or SNP or combination thereof, have been compared to the parental lines. The comparisons carried out included phenotyping of inflorescence types and tomato fruit related traits.

All tomato lines have been grown in soil, in a commercial-type greenhouse during the spring-summer season at Ganei Tal, Israel, without any extension of natural day length (i.e. 12-14 hrs of light). Minimum growth temperature is 12° C., and fertilization (5-3-8 N-P-K) was applied through the drip-irrigation system. Planting was preferably performed in 8 blocks, 5 plants of each genotype per block. The following data was recorded i.e. for the 3rd, 5th and 7th clusters:

Time to first open flower.
Number of flowers and mature fruit of commercial size for each cluster.
Time until the first mature fruit for each cluster.

Mature fruits were harvested from all plants 3-4 times during the trial. The harvesting may began 5-7 days after the first fruit reached breaker as defined hereinabove, and preferably may continue until all mature fruits from clusters 2 through 8 are picked. In other embodiments all mature fruits are harvested regardless of cluster number. In a further embodiment, if the data is collected by cluster, clusters are harvested once the first fruit maturates. According to certain embodiments, harvesting began about one week after the first fruit reached breaker and with about one week interval between harvests. Yield parameters evaluated included the number of mature fruits harvested from each plant, the weight of mature fruits per plant, individual mature fruit weight and a total soluble solids measurement i.e. measuring of about 12 representative mature fruits from each plant (three from each harvest), In a further embodiment all the fruits of commercial size were harvested and their average individual weight was calculated.

Reference is now made to Table 6, presenting the results of the analysis of the F1 hybrid 3291, resulting from a cross between 4468 donor plant having a branching inflorescence phenotype and 4466 recipient plant having a normally branched inflorescence.

TABLE 6

Yield parameters of 3291 hybrid population

| Genotype | | Mean | Std Error | Prob > F | Column A | Column B | Column C |
|---|---|---|---|---|---|---|---|
| Number of fruits | 3291 | 26.35 | 2.09 | 2.37E−06 | A | | |
| | 4468 | 22.53 | 2.03 | | A | | |
| | 4466 | 9.53 | 2.15 | | | B | |
| Total fruits weight (kg) | 3291 | 2.57 | 0.19 | 4.78E−07 | A | | |
| | 4468 | 1.77 | 0.18 | | | B | |
| | 4466 | 0.87 | 0.19 | | | | C |
| Average fruit weight (gr) | 4466 | 96.36 | 5.95 | 0.0787 | A | | |
| | 3291 | 96.22 | 5.41 | | A | | |
| | 4468 | 79.19 | 4.87 | | A | | |
| Average fruit brix/plant | 4466 | 6.26 | 0.11 | 2.72E−09 | A | | |
| | 3291 | 5.41 | 0.10 | | | B | |
| | 4468 | 5.27 | 0.10 | | | B | |
| Brix X Yield | 3291 | 13.82 | 1.03 | 1.99E−06 | A | | |
| | 4468 | 9.38 | 1.00 | | | B | |
| | 4466 | 5.28 | 1.10 | | | | C |

The results of Table 6 are summarized in Tables 7 and 8. Reference is now made to Table 7 showing average fruit yield per plant and average brix*yield in normally branched 4466 genotype as compared to the heterozygous plants of 3291. As can be seen, the yield per plant is increased by about 194% in the heterozygous plants (+/−) as compared to the normally branched plants (−/−). The heterotic effect of the plants having heterozygous configuration of the branching inflorescence trait is also observed with respect to the brix*yield parameter. The brix*yield of the hybrid plants of the present invention is about 1.5 fold higher than the normally branched parental line.

TABLE 7

Summary of yield parameters of 3291 genetic background

| | Average fruit yield/plant (gr) | | | | Average Brix * Yield | | | |
|---|---|---|---|---|---|---|---|---|
| Genetic background | −/− | −/+ | Yield/plant increase (%) | Significance level | −/− | −/+ | Brix * Yield increase (%) | Significance level |
| 3291 | 871 | 2565 | 194% | **** | 5.27 | 13.81 | 162% | **** |

*—significance level <0.1
**—significance level <0.05
***—significance level-<0.01
****—significance level <0.001

Reference is now made to Table 8 showing average individual fruit weight and average individual fruit brixs (TSS) in normally branched 4466 compared with the 3291 heterozygous plants. As can be seen, the heterozygous plants having a branching inflorescence phenotype (−/+) produce high yield of fruits characterized by individual fruit weight which is similar to the values of the normally branched (−/−) 4466 parent.

TABLE 8

Summary of individual fruit parameters of 3291 genetic background

| Genetic background | Average individual fruit weight (gr) | | Significance level |
|---|---|---|---|
| | −/− | +/− | |
| 3291 | 96.4 | 96.2 | n.s. |

\* significance level < 0.1
\*\* significance level < 0.05
\*\*\* significance level-< 0.01
\*\*\*\* significance level < 0.001
n.s.—not significant Reference is now made to Table 9, presenting yield results of F2 plants from the population that was used for the breeding of 4468, the donor of the branched inflorescence type.

TABLE 9

Yield parameters of F2 plants as compared to parental plants

| plant | # of fruits per plant | Brix * yield | Total fruits weight/ plant (kg) | Average fruit brix | Average fruit weight (gr) | Marker haplotype (based on SNP7) |
|---|---|---|---|---|---|---|
| 3582-24 | 36.77134 | 20.90568 | 3.69129 | 5.62829 | 107.34 | H |
| 3528-15 | 38.0557 | 16.73755 | 3.44091 | 4.90848 | 90.61 | H |
| 3555-7 | 39.87953 | 18.33305 | 3.37788 | 5.57022 | 83.06 | H |
| 3555-7 | 39.87953 | 18.33305 | 3.37788 | 5.57022 | 83.06 | H |
| 3501-20 | 41.03832 | 18.63932 | 4.01078 | 4.6832 | 98.38 | H |
| 3501-21 | 41.03832 | 21.91579 | 4.41978 | 5.0082 | 109.38 | H |
| 3582-7 | 44.77134 | 24.65414 | 4.64829 | 5.25496 | 109.34 | H |
| 3501-12 | 60.03832 | 26.99319 | 5.34878 | 5.1082 | 87.38 | H |
| 3565-16 | 5.94903 | 2.6838 | 0.63522 | 4.97718 | 83.29 | R |
| 3592-25 | 10.40681 | 6.50932 | 1.08536 | 5.80632 | 114.19 | R |
| 3538-4 | 10.58054 | 4.6406 | 1.08621 | 4.85376 | 84.3 | R |

Marker legend:
H—heterozygote;
R—regular or normal

Table 9 presents F2 plants expressing the desired phenotype of high yield per plant combined with individual fruit weight and/or fruit brix.

Thus the results above demonstrate that the present invention provides tomato plants with diverse genetic backgrounds having the unique characteristics of exhibiting a branching inflorescence phenotype, combined with the production of statistically significant high yield of mature fruits having the characteristics of average individual fruit weight and/or average individual fruit brix levels similar to fruits produced by a tomato line that is used as the normally branched parent line of said tomato plant.

Example 4

Identifying Novel Molecular Markers

The characterization of plants with the desirable specific statistically significant high yield properties was preferably based upon identification of genetic markers. Molecular assays were performed to identify genetic markers associated with the branching inflorescence introgression allele leading to the unique statistically significant high yield phenotypic characteristics of the tomato plants. These markers were essential for the production of stable and commercially valuable statistically significant high yield cultivated tomato plants, characterized by statistically significant increased fruit weight, while unexpectedly maintaining individual fruit weight as the tomato line lacking the branching inflorescence introgression, used as the normal or regular branched parent line of said tomato plant.

According to certain embodiments, the KASPar genotyping method was used. The KASPar genotyping method is based upon allele-specific amplification followed by fluorescence detection.

It is within the scope of the present invention that certain variations are made in the KASPar genotyping method, including the detailed below protocols used in the present invention.

The present invention provides novel genetic markers that are herein shown to identify tomato plants having the unique commercially desirable statistically significant high yield properties of increased number of fruits without having the commonly known expense of reduced individual fruit weight and/or fruit brix values.

Reference is now made to Tables 10, 11 and 12 showing newly identified molecular markers and their informative capacity with respect to identifying branching versus regular or normal type inflorescence phenotype and with respect to the presence of the unique statistically significant increased fruit yield properties as described in Examples 2 and 3. The molecular markers were screened in several genetic backgrounds, including, but not limited to, 4131 elite breeding line, Hazera's germplasm breeding line 64, breeding line 60, breeding line 160, HAG1 and 4468 line of the Roma background. These tomato lines are described according to selected UPOV definitions in Table 2 and are used as examples of plants used to produce the hybrid plants with the improved yield characteristics.

As shown in Table 10, an Indel marker segregating with the branching inflorescence allele associated with the specific statistically significant high yield of fruit weight phenotype (i.e. obtainable from HAG 1 as a donor) was identified. This novel informative Indel is a marker of 271 bp nucleotide sequence corresponding to the nucleotide sequence as set forth in SEQ ID NO: 5. It was found that the presence or absence of the Indel marker is linked with the presence or absence of a branching inflorescence allele that is associated with the specific and unique statistically significant high fruit yield characteristics. The Indel marker as presented inter alia was identified mainly by using the following steps:

Primers were designed based on the tomato genome reference sequence SL2.40ch02:36896083..36900744. A forward primer comprising the nucleotide sequence corresponding to the nucleotide sequence as set forth in SEQ ID NO:1 is positioned about 2,283 bp to 2,307 bp in the reference tomato genome region>SL2.40ch02: 36896083..36900744. According to a preferred embodiment, the nucleotide sequence of the forward primer is detailed herewith:

```
Forward:
                                    (SEQ ID NO: 1)
5' TGTCACCAAGCTCTGAGCATCATT 3'
```

A reverse primer having the nucleotide sequence corresponding to the nucleotide sequence as set forth in SEQ ID NO:2 was designed. In a specific embodiment, the reverse primer is positioned about 3,235 bp to 3,257 bp in the reference tomato genome region>SL2.40602: 36896083..36900744, and preferably has the nucleotide sequence as detailed herewith:

Reverse:

(SEQ ID NO: 2)
5' TGACTCCCCAATGTAACCGCCA 3'

According to another embodiment, a PCR reaction was performed using a first primer having the polynucleotide sequence corresponding to the polynucleotide sequence as set forth in SEQ ID NO:1 and a second primer having the polynucleotide sequence corresponding to the polynucleotide sequence as set forth in SEQ ID NO:2. An example of such a PCR reaction could be a reaction carried out in about 25 µl volume containing about 50 ng genomic DNA, about 50 mM KCl, about 10 mM Tris-HCl, about 2 mM MgCl2, about 0.2 mM of each dNTP, about 0.4 µM of each primer (i.e. forward and reverse primers), and about 1 unit Taq polymerase (i.e. Fermentas). In some specific embodiments, the PCR might be performed using a thermocycler with cycling conditions such as 95° C. 3 min, (95° C. 30 sec, 60° C. 30 sec, 72° C. 90 sec) repeated 35 cycles followed by 72° C. for 7 min.

According to other certain embodiments, the produced PCR products were analyzed by gel electrophoresis, preferably using 2% agarose gel in 1 TAE buffer.

In one embodiment, it was found that a DNA segment in a length of about 974 bp having a polynucleotide sequence corresponding to the nucleotide sequence as set forth in SEQ ID NO:3 is co-segregating with the absence of a branching inflorescence allele (i.e. obtainable from HAG1) associated with the unique high fruit yield properties as herein disclosed. Such a DNA fragment includes the Indel marker having the nucleotide sequence corresponding to the sequence as set forth in SEQ ID NO:5 and is designated "+" in Table 10.

In another embodiment, a DNA segment in a length of about 703 bp having a polynucleotide sequence corresponding to the nucleotide sequence as set forth in SEQ ID NO:4 was herein found to co-segregate with the presence of a branching inflorescence allele obtainable of HAG1 branching inflorescence source, associated with the unique and specific statistically significant high fruit yield properties as herein disclosed. Such a DNA fragment lacks the Indel marker having the nucleotide sequence corresponding to the sequence as set forth in SEQ ID NO:5 and is designated "−" in Table 10. Note that line 4468 of the Roma type is identified by the molecular markers, as having a regular inflorescence phenotype, but, as will be shown below, such branching inflorescences are genetically identified by a different set of novel markers (see Table 11).

Thus, according to certain embodiments of the invention, the presence of DNA segments having the nucleotide sequence corresponding to the nucleotide sequence as set forth in SEQ ID NO:3 and SEQ ID NO:4, is indicative of a plant having a branching inflorescence phenotype, and having the unique properties of statistically significant high fruit yield (as shown in Examples 2 and 3).

It is evident by the results of the present invention that a novel Indel marker of about 271 bp, having the nucleotide sequence corresponding to the nucleotide sequence as set forth in SEQ ID NO. 5 is indicative of a branching inflorescence allele, obtainable of HAG1 branching inflorescence source, herein shown to be linked with statistically significant increased fruit weight, when it is presented in heterozygous configuration in a genome of a plant. Such an Indel marker is used herein as a genetic tool to produce and identify the plants of the present invention, having a branching inflorescence phenotype, surprisingly associated with desirable and commercially valuable specific high fruit yield properties as herein disclosed.

According to a further embodiment, single nucleotide polymorphisms (SNPs) were identified that are co segregating with the branching inflorescence allele obtainable of HAG1 branching inflorescence source, revealed to be associated with the unique high fruit yield properties as defined in Example 2. SNP1 is positioned 2,197 bp in the reference tomato genome region>SL2.40ch02:36916358..36912768 as set forth in the nucleotide sequence corresponding to the nucleotide sequence as set forth in SEQ ID NO:6.

As shown in Table 10, the novel SNP1 marker is able to discriminate between plants lacking the branching inflorescence allele, obtainable of HAG1 branching inflorescence source, revealed to be associated with the unique statistically significantly increased fruit yield properties, and tomato plants comprising the aforementioned branching inflorescence allele.

Additional novel single nucleotide polymorphisms were revealed to identify, in combination, tomato plants having the specific phenotype of branching inflorescence associated with increased weight of mature fruits. SNP2 is positioned 2,161 and SNP6 is position 2,146, both in the reference tomato genome region>SL2.40ch02:36904300..36901545 having the nucleotide sequence corresponding to the nucleotide sequence as set forth in SEQ ID NO:7.

According to certain embodiments of the invention, the combination of both SNP2 and SNP6 is uniquely informative to tomato plants harboring the branching inflorescence allele, obtainable of HAG1 branching inflorescence source, associated with the unique statistically significant high fruit yield properties disclosed in Example 2 of the disclosure.

It is emphasized that the novel Indel and SNP markers disclosed for the first time by the present invention, are shown to specifically identify and select tomato plants having the specific phenotypic characteristics of a branching inflorescence uniquely associated with statistically significant increased yield of fruit weight as compared to tomato lines lacking the branching inflorescence trait. It is therefore a main aspect of the present invention to provide novel informative genetic markers that are used alone (such as the Indel and SNP1) or in combination (SNP2 and SNP6), to produce the statistically significant high yield tomato plants of the present invention.

TABLE 10

Screening results using the novel molecular markers of the present invention

| Presence of a branching inflorescence allele | line | SNP1 | SNP2 | SNP6 | Indel |
|---|---|---|---|---|---|
| − | Line 64 Breeding line | C | C | A | + |
| − | Line 60 Breeding line | C | C | A | + |
| − | 4131 Recipient elite line | C | T | T | + |
| + | HAG1 Donor line | A | C | T | − |
| + | 1403 (line 4131 background) Advanced line | A | C | T | − |
| + | 1406 (line 60 background) Advanced line | A | C | T | − |

TABLE 10-continued

Screening results using the novel molecular markers of the present invention

| Presence of a branching inflorescence allele | line | SNP1 | SNP2 | SNP6 | Indel |
|---|---|---|---|---|---|
| + | 1408 (line 64 background) Advanced line | A | C | T | − |
| + | 160 (Roma background) Breeding line | A | C | T | − |
| + | 4468 (Roma background) Breeding line | C | C | A | + |

It is noted that the screening results summarized in Table 10 revealed a branching inflorescence phenotype, demonstrated by line 4468 of the Roma type that is identified by the molecular markers detailed in the aforementioned table, as having a regular inflorescence phenotype.

Thus, in certain aspects of the present invention, molecular assays were performed to identify additional novel genetic markers or novel genetic marker combinations cosegregating with a branching inflorescence phenotype.

These novel markers could identify additional branching inflorescence phenotypes associated with beneficial statistically significant high yield traits, i.e. originating from the 4468 Roma line.

Reference is now made to Table 11, describing novel molecular markers that were found to be informative for the aforementioned novel branching inflorescence phenotype: (1) SNP7, positioned 2,313 in the reference tomato genome region>SL2.40ch02:36904300..36901545 as set forth in SEQ ID NO:7; (2) SNP14 positioned 1589 in the reference tomato genome region>SL2.40ch02:36904300..36901545 as set forth in SEQ ID NO:7.

According to one embodiment, the presence of SNP7 could uniquely identify the branching inflorescence phenotype which is associated with the statistically significant high yield characteristics demonstrated and obtainable by line 4468 of the Roma genetic background.

According to a further embodiment of the invention, the presence of SNP14, could uniquely identify the branching inflorescence phenotype which is associated with the statistically significant high yield characteristics demonstrated and obtainable by line 4468 of the Roma genetic background.

TABLE 11

Identifying novel molecular markers combinations

| Presence of a branching inflorescence allele | line | SNP7 | SNP14 |
|---|---|---|---|
| − | Line 64 Breeding line | T | T |
| − | Line 60 Breeding line | T | T |
| − | 4131 Recipient elite line | T | T |
| + | HAG1 Donor line | T | T |
| + | 1403 (line 4131 background) Advanced line | T | T |
| + | 1406 (line 60 background) Advanced line | T | T |
| + | 1408 (line 64 background) Advanced line | T | T |
| + | 160 (Roma background) Breeding line | T | T |
| + | 4468 (Roma background) Breeding line | C | A |

Reference is now made to Table 12 describing unique haplotypes provided by the present invention to identify and screen for tomato plants having branching inflorescence phenotype. This genetic source material is shown by the present invention for the first time to be commercially valuable for the production of high yield tomato plants.

The unique haplotypes include the combination of the Indel marker and SNP7 or the combination of the Indel marker and SNP14. The aforementioned marker combinations can distinguish between a normally branched plant, a branching inflorescence plant obtainable by line 4468 of the Roma genetic background, and a branching inflorescence plant obtainable by HAG1.

TABLE 12

Unique haplotypes for identifying branching inflorescence phenotype

| Presence of a branching inflorescence allele | line | SNP7 | SNP14 | Indel |
|---|---|---|---|---|
| − | Line 64 Breeding line | T | T | + |
| − | Line 60 Breeding line | T | T | + |
| − | 4131 Recipient elite line | T | T | + |
| + | HAG1 Donor line | T | T | − |
| + | 1403 (line 4131 background) Advanced line | T | T | − |
| + | 1406 (line 60 background) Advanced line | T | T | − |
| + | 1408 (line 64 background) Advanced line | T | T | − |
| + | 160 (Roma background) Breeding line | T | T | − |
| + | 4468 (Roma background) Breeding line | C | A | + |

According to one embodiment, the combination of the absence of the Indel marker ("−" in Table 12) and A/T at the position of SNP7 or SNP14 could uniquely identify the branching inflorescence phenotype which is associated with the statistically significant high yield characteristics obtainable by HAG1.

According to a further embodiment of the invention, the presence of the Indel marker ("+" in Table 7) and C/G at the position of SNP7, and/or A/T at the position of SNP14 could uniquely identify the branching inflorescence phenotype which is associated with the statistically significant high yield characteristics demonstrated by line 4468 of the Roma genetic background.

In fact, the molecular marker combinations described in Table 12 could identify at least two different types of branching inflorescence phenotype that are herein shown to be associated with statistically significant improved yield of fruits.

Thus, it is evident by the results disclosed herein that the present invention provides novel and unique molecular markers cosegregating with a branching inflorescence trait. These biomarkers include genetic markers identifying a branching inflorescence phenotype surprisingly associated with statistically significant high fruit yield properties such as increased fruit weight with desirable individual fruit weight and/or fruit brix and/or earliness parameters as compared to tomato lines used as the normal or regular branched parent line of said tomato plant. Therefore, the markers of Tables 10-12 are useful in detecting high fruit yield plants, which exhibit branching inflorescence phenotype, and screening out low fruit yield plants.

The invention claimed is:

1. A tomato plant exhibiting a branching inflorescence phenotype of at least 7 flowers per inflorescence, wherein said plant comprises an introgressed branching inflorescence associated haplotype comprising a single nucleotide polymorphism of C at position 2,313 in SEQ ID NO:7, said branching inflorescence phenotype is found when said introgressed haplotype is in a heterozygous configuration, said haplotype is as found in Solanum lycopersicum 4468, representative seed of which was deposited with NCIMB Aberdeen AB21 9YA, Scotland, UK on Apr. 11, 2012 under accession number NCIMB 41957, further wherein said tomato plant produces a statistically significant increased average fruit weight yield per plant of at least 8% as compared to the yield of a tomato line having the same genetic background and lacking said haplotype, said fruits of said tomato plant having the characteristics of average individual fruit weight or average individual fruit brix levels or a combination thereof, with resemblance range of ±20% to fruits produced by said tomato line having the same genetic background and lacking said haplotype.

2. The tomato plant according to claim 1, wherein said haplotype further comprises a polynucleotide sequence as set forth in SEQ ID NO:3.

3. The tomato plant according to claim 1, wherein said plant has at least one characteristic selected from the group consisting of: mature fruits with average individual brix level of at least 4 units, mature fruits with average individual weight of at least 90 gr, increased average fruit weight yield per cluster of at least 10% as compared to the yield per cluster of said tomato plant line having the same genetic background and lacking said haplotype, increased average flower number per cluster of at least 20% as compared to the average flower number per cluster of said tomato line having the same genetic background and lacking said haplotype, having an average number of at least 20 fruits per plant, a decrease of at least 15% in the average number of days to first ripen fruit as compared to said tomato line having the same genetic background and lacking said haplotype, and wherein said plant is a hybrid.

4. The tomato plant according to claim 1, wherein said haplotype comprises a combination of: said single nucleotide polymorphism at position 2,313 in SEQ ID NO:7 combined with a 271 bp indel marker having a nucleotide sequence as set forth in SEQ ID NO:5.

5. A plant part comprising at least one regenerable cell, pollen, ovule, fruit or seed of the tomato plant according to claim 1, said cell, pollen, ovule, fruit and seed comprise the heterozygous configuration of said branching inflorescence associated haplotype of a single nucleotide polymorphism of C at position 2,313 in SEQ ID NO:7.

6. A tomato seed (a) obtained from a crossing in which at least one of the parents is the tomato plant according to claim 1 or (b) which produces the tomato plant of claim 1, wherein said seed of (a) or (b) comprises heterozygous configuration of said branching inflorescence associated haplotype.

7. The seed according to claim 5, wherein a plant grown from the seed produces a tomato plant exhibiting a branching inflorescence phenotype co-segregating with said haplotype comprising a single nucleotide polymorphism of C at position 2,313 in SEQ ID NO:7, said plant comprises heterozygous configuration of said haplotype, wherein said plant produces a statistically significant increased average fruit weight yield per plant of at least 8% as compared to the yield of a tomato line having the same genetic background and lacking said haplotype, said fruits having the characteristics of average individual fruit weight or average individual fruit brix levels or a combination thereof, with resemblance range of ±20% to fruits produced by said tomato line having the same genetic background and lacking said haplotype.

8. The tomato plant according to claim 1, wherein said plant further comprising within its genome at least one additional trait selected from the group consisting of herbicide resistance, insect resistance, resistance to bacterial, fungal or viral disease, and resistance to a non-biotic stress, wherein the additional trait is introduced by a method selected from the group consisting of breeding, genetic determinant introgression and transformation.

9. A tissue culture of regenerable cells, protoplasts or callus obtained from the tomato plant according to claim 1.

10. A method for producing a tomato plant exhibiting a branching inflorescence phenotype of at least 7 flowers per inflorescence, wherein said plant comprises an introgressed branching inflorescence associated haplotype comprising a single nucleotide polymorphism of C at position 2,313 in SEQ ID NO:7, said branching inflorescence phenotype is found when said introgressed haplotype is in a heterozygous configuration, said haplotype is as found in Solanum lycopersicum 4468, representative seed of which was deposited with NCIMB Aberdeen AB21 9YA, Scotland, UK on Apr. 11, 2012 under accession number NCIMB, further wherein said plant produces a statistically significant increased average fruit weight yield per plant of at least 8% as compared to the yield of a tomato line having the same genetic background and lacking said haplotype, said fruits having the characteristics of average individual fruit weight or average individual fruit brix levels or a combination thereof, with resemblance range of ±20% to fruits produced by said tomato line having the same genetic background and lacking said haplotype, said method comprising the steps of:

a. selecting a first tomato plant having a branching inflorescence phenotype of at least 10 flowers per inflorescence, wherein said plant comprises a homozygous configuration of said haplotype of a single nucleotide polymorphism of C at position 2,313 in SEQ ID NO:7, further wherein said haplotype is as found in Solanum lycopersicum 4468, representative seed of which was deposited with NCIMB Aberdeen AB21 9YA, Scotland, UK on Apr. 11, 2012 under accession number NCIMB 41957, and a second tomato plant lacking said haplotype;

b. crossing the first and the second tomato plants of step (a) to produce an F1 tomato plant progeny;

c. analyzing a DNA sample obtained from the progeny of step (b) for the presence of a heterozygous configuration of said branching inflorescence associated haplotype of a single nucleotide polymorphism of C at position 2,313 in SEQ ID NO:7;

d. selecting at least one plant having the characteristics of step (c) and having at least 7 flowers per inflorescence; and e. evaluating fruit yield parameters of said progeny of step (d), and selecting at least one plant producing a statistically significant increased average fruit weight yield per plant of at least 8% as compared to the yield of a tomato line having the same genetic background and lacking said branching inflorescence associated haplotype, said fruits having the characteristics of average individual fruit weight or average individual fruit brix levels or a combination thereof, with resemblance range of ±20% to fruits produced by said tomato line having the same genetic background and lacking said branching inflorescence associated haplotype.

11. The method according to claim 10, comprising an additional step of selfing the F1 tomato plants of step (b) to produce F2 tomato plant progeny, optionally selfing at least once said F2 progeny to produce F3 plants and optionally backcrossing at least once said F1 and/or said F2 plants with at least one tomato line lacking said haplotype and repeating step (d) of selecting at least once.

12. The method according to claim 10, comprising an additional step of introducing into the genome of said plant at least one trait selected from the group consisting of: herbicide resistance, insect resistance, resistance to bacterial, fungal or viral disease, resistance to non-biotic stress and any combination thereof.

13. The method according to claim 10, further comprises the step of:
f. analyzing said DNA for the presence of said single nucleotide polymorphism at position 2,313 in SEQ ID NO:7 combined with a 271 bp indel marker having a nucleotide sequence as set forth in SEQ ID NO:5, wherein the presence of C at the position 2,313 of SEQ ID NO:7 combined with the presence of a 271 bp indel marker having a nucleotide sequence as set forth in SEQ ID NO:5 is further indicative of a plant having a branching inflorescence phenotype.

14. The method according to claim 10, further comprising additional steps of:
f. amplifying a DNA segment using a first primer having a polynucleotide sequence as set forth in SEQ ID NO:1 and a second primer having a polynucleotide sequence as set forth in SEQ ID NO:2; and,
g. analyzing the amplified DNA segments produced by the amplification of step (f), wherein the presence of a DNA segment having a polynucleotide sequence as set forth in SEQ ID NO:3 is further indicative of a plant having a branching inflorescence phenotype, wherein said plant produces a statistically significant increased average fruit weight yield per plant of at least about 8% as compared to the yield of a tomato line having the same genetic background and lacking said haplotype, said fruits having the characteristics of average individual fruit weight or average individual fruit brix levels or a combination thereof, with resemblance range of ±20% to fruits produced by said tomato line having the same genetic background and lacking said haplotype.

15. The plant according to claim 1, wherein said single nucleotide polymorphism is used in marker based selection of a tomato plant exhibiting a branching inflorescence phenotype of at least 7 flowers per inflorescence, wherein said plant produces a statistically significant increased average fruit weight yield per plant of at least 8% as compared to the yield of a tomato line having the same genetic background and lacking said haplotype, said fruits having the characteristics of average individual fruit weight or average individual fruit brix levels or a combination thereof, with resemblance of ±20% to fruits produced by tomato line having the same genetic background and lacking said haplotype.

16. A tomato plant exhibiting a branching inflorescence phenotype of at least 10 flowers per inflorescence, wherein said plant comprises a homozygous configuration of a haplotype comprising a single nucleotide polymorphism of C at position 2,313 in SEQ ID NO:7, said haplotype is as found in *Solanum lycopersicum* 4468, representative seed of which was deposited with NCIMB Aberdeen AB21 9YA, Scotland, UK on Apr. 11, 2012 under accession number NCIMB 41957, further wherein said tomato plant when crossed with a tomato plant lacking said haplotype, provides a progeny tomato plant heterozygous for said haplotype, said progeny plant exhibiting a branching inflorescence phenotype of at least 7 flowers per inflorescence and producing a statistically significant increased average fruit weight yield per plant of at least 8% as compared to the yield of a tomato line having the same genetic background and lacking said haplotype, said fruits of said tomato plant having the characteristics of average individual fruit weight or average individual fruit brix levels or a combination thereof, with resemblance range of ±20% to fruits produced by said tomato line having the same genetic background and lacking said haplotype.

* * * * *

```
                            SEQUENCE LISTING

<160> NUMBER OF SEQ ID NOS: 7

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
tgtcaccaag ctctgagcat catt                                           24

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
tgactcccca atgtaaccgc ca                                             22

<210> SEQ ID NO 3
<211> LENGTH: 974
<212> TYPE: DNA
<213> ORGANISM: Solanum lycopersicum

<400> SEQUENCE: 3
tgtcaccaag ctctgagcat catttgtttc cattaagatt aagacatctg aatctgaata    60
ttaagatatg cattaaaatc tagatgtgta aatctaaata aacatctgaa tattaaaatg   120
ttgtctctga atctgaacac tgaattattg gaactgtttg tttttaatat ctgaatgtac   180
atatgaatta gaacgctata taaataagat attataaaaa cctcatttta gtaaaatatt   240
ttttttatat agaaaataat gttttcaaca ttcttatcgt aacaaggtaa tgtgatttat   300
ttattaagaa tttaatatta cgttacatca ttaatatgac tattctttgt actcaaaaac   360
tttgagaatc taatataatg caatgtaaaa tagtttaaac aaaatagtaa tataatgttt   420
atgaaaacat tttattttat aatggacatt tgttattgtt attgatcaaa taattatact   480
ttcttatttt ctgaaattat gctaaatatt atatcatgaa gtgcttatca attcaaataa   540
attgattaat ttatgaaagt aaaagatgta tattaagtta gtaagaataa aggaaattgg   600
taaacatgta attaaataag aaaatatttt ttatgagttg ttgtgatgca gttgaattaa   660
tataggggtt ctatttttga gtctcactga tgatatgaaa aggtgttaca tatctgattc   720
attcaaacgt attcagacct attaagagaa ttagaagaaa ataaaataat caaatttaat   780
```

```
gaactaaatt tgaataatta aaatttaatt ctaaaaataa acgcactaaa taaagtgaat      840
ctctgatcga ttagaattca atcccatta  agtaaaaaaa aaaaaaaaag aaaagtagag      900
gcctaatctc ttttcttaaa aaataatact ccatattgta ttttttttta tatggcggtt      960
acattgggga gtca                                                        974
```

```
<210> SEQ ID NO 4
<211> LENGTH: 703
<212> TYPE: DNA
<213> ORGANISM: Solanum lycopersicum

<400> SEQUENCE: 4
tgtcaccaag ctctgagcat catttgtttc cattaagaat ttaatattac gttacatcat       60
taatatgact attctttgta ctcaaaaact tgagaatct  aatataatgc aatgtaaaat      120
agtttaaaca aaatagtaat ataatgttta tgaaaacatt ttattttata atggacattt      180
gttattgtta ttgatcaaat aattatactt tcttattttc tgaaattatg ctaaatatta      240
tatcatgaag tgcttatcaa ttcaaataaa ttgattaatt tatgaaagta aagatgtat       300 attaagttag taagaataaa ggaaattggt aaacatgtaa ttaaataaga aaatattttt      360
tatgagttgt tgtgatgcag ttgaattaat ataggggttc tattttttgag tctcactgat      420 gatatgaaaa ggtgttacat atctgattca ttcaaacgta ttcagaccta ttaagagaat      480
tagaagaaaa taaataatc  aaatttaatg aactaaattt gaataattaa aatttaattc      540
taaaaataaa cgcactaaat aaagtgaatc tctgatcgat tagaattcaa atcccattaa      600
gtaaaaaaaa aaaaaaaga  aaagtagagg cctaatctct tttcttaaaa aataatactc      660
catattgtat ttttttttat atggcggtta cattggggag tca                        703
```

```
<210> SEQ ID NO 5
<211> LENGTH: 271
<212> TYPE: DNA
<213> ORGANISM: Solanum lycopersicum

<400> SEQUENCE: 5
ttaagacatc tgaatctgaa tattaagata tgcattaaaa tctagatgtg taaatctaaa       60
taaacatctg aatattaaaa tgttgtctct gaatctgaac actgaattat tggaactgtt      120 tgttttaat  atctgaatgt acatatgaat tagaacgcta tataataag  atattataaa      180 aacctcattt tagtaaaata ttttttttat atagaaaata atgttttcaa cattcttatc      240
gtaacaaggt aatgtgattt atttattaag a                                     271
```

```
<210> SEQ ID NO 6
<211> LENGTH: 3591
<212> TYPE: DNA
<213> ORGANISM: Solanum lycopersicum
<220> FEATURE:
<221> NAME/KEY: mutation
<222> LOCATION: (2197)..(2197)
<223> OTHER INFORMATION: SNP1

<400> SEQUENCE: 6
ttattttgaa tttaagagct ttcactgtct ttcactctga tgaagattct aatataagcc       60
ccatcatgtg cttctttcaa tgttctcttt gttttctctt caaattgaac taattgggct      120
ttttgttaca ttgagtagtg aacaagtatt ttcagtctga aatataataa ttttgtgaac      180
aagttataat tataagggta tgggccatgt actagatctc tagtctatct ttttcacttt      240
```

```
acatttaatt tcatttctat ttttgtttat catttaacag gtgattcttg ttttgggttt      300 tgtcttttt  atttctacaa tttgttttct ttaatccta  aaaaaaaag  aaaagagtag      360 taggtatgga gtctatataa gaagtgtgtt agggttgttt atagactacc aaaaaaaaaa      420
agcttaaaga gagttacctt ttttatttc  ttcttcatcc tcatcaaata tggcttcatc      480
aaatagacac tggcctagta tgtttaaatc caaaccttgc aattctcatc atcaccaatg      540
gcaacatgac atcaactctt ctatcattca acaaagacct ccatgcaatc caggtacata      600
tatatatata tatatatatt tacatttctt ttttcttttg taatgaatga ggttttgatt      660
taaatttttt ttataataat tatgattaga agagcgaagt ccagagccaa agcctcgatg      720
gaatccaaga cctgagcaaa ttcgtatact tgaagcaatc tttaattcag gcatggtgaa      780
tccaccaagg gatgagataa ggaaaatccg agctaaactt caagaatatg gtcaagtagg      840
tgatgctaat gtgttttact ggtttcaaaa caggaaatca agaagtaaac acaaacaacg      900
tcatttacaa gctaaagctc aacaacaaca ccataataat aacaataatt catctcatca      960
acctattatt acttcatctt catcatcttc tgataaatct tcaccaaatt cattgacttt     1020
ctcaattggt acctccaatg ttatggactt gctcaattct cctacttctt cggtgaacca     1080
acaaaactat aacgagttcc tgtctaacga gcagcctttc tttttcactg tacaaccacc     1140
accagtagta ccaactcatg atcactccgc agggttttgc ttccaggatt catctacttt     1200
tactcctcat tcttcttctt ctggacttct tcttaatgaa tggatggggg ggataagtac     1260
tcaagcacct aataattcaa agaaagatga aaatgacaaa atcaatttgc agtcacagct     1320
catgagttat acagttactt caactgtttc tcctcttgct actaccacta ttcccaccat     1380
tagtcacatt caaggtaagc cttttactca ctcttcatcc gttacatttt atatgatact     1440
ttttttttaa ccgtttccaa atatcacaag ttttaaggat attttttattt tttattttca     1500 tttaaatcta tgtatcgtca aatactatca tataaattga acattaaaa  caacggaaaa     1560 aaaaatagag tagggagga  ctattgagta actgaaaatg ctaatttatt tacttttttt     1620
ttaaaaaaaa tgttgagtat gtggtgggct agctactcag tacaaatgat accatatcta     1680
gtatgaatgt gcactttaac attttttttcc attaacttca tgacaaaagt gaagatatat     1740
aaatagagtc tagaaagttg aaagccactc attttatttt attttagggc cagaactgag     1800
aatgagaata aatgtttgtc tctattcata cgaaatttaa tcataataag taaaatcttc     1860
cactggcatt tcatggaagt gattgatgct atgctaggcc tgttcacttt ttacacagtg     1920
ttctttttaa caaaggctaa taaagtagtt ttacattttc tcatacgtta tgttttatag     1980
ataagacaag gttagatttg tcctttggct tcctcatttt ctgatttctt gtctacattt     2040
tttttgtgaa caaacgttcg catggatgga ttttttggat ttatgtatat ataaaattga     2100
ctactgcatt ggttacattt atctcatgat tgtgtaacgt acgtgtggtt gtagggtta      2160 ctgtggatcc taatgatgcg ggtcccacaa gatcgacagt gtttatcaac gacgttgctt     2220
ttgaggttgg gataggaccg tttaacgtga gggaagtgtt cggtgaagat gcggtgctta     2280
tacattcatc tggtgaacca cttattacta atgaatgggg tatcacaatt cagccactac     2340
agcatggtgc atttactac  ttgcttcgca cgtcaagtat tgcatcgact catcatatat     2400
aacggagaca taattgattt ggtacgaatt caaattttta ttatatttttt taacattgca     2460 cattataaaa cctttctagg aaatactttt ttttatttttg attaaaaatc atatttgact     2520
gcagatttgt tgatgttgaa gaagaaaaag atgtttggtg ttgtgttttg tttcattgtc     2580
tcttgaagaa aagaaggagg ggggggggg  gttaattagt ttaatttgta gtgttaatta     2640
```

-continued

```
gtatgttact ttaagggaca ttttagttat tacagaaatc taattaagtc cttagtcaat    2700
gtgtactatg tttcatttttt ttatgatgaa atgaaactaa caaattatta tattataata    2760
taaatgcgcc tttttgaggt ttaattactt tattttgatg atacaaataa gttgattaat    2820
tagtaaaatg gatgacttca gttgcatttt tatttatttt tacatgtgat gatatatatg    2880
tgtctatgaa ggtgaagaaa aaatccaata actgtgatat catcattaac atattttctg    2940
gcagctttca tgtttacttg tttgcttatt ctgcaaggaa agcaaagcat ggttgctgta    3000
attaagtgcc tttattttca ttttatacct tattataagt ttaagttatg cacgttatta    3060
tcgcgataaa ctaactcatg ttaaaattta atcacacatt ctaaggatta cttataagta    3120
aaaaaatctc atgcgactag ctagataaga aagctactaa tacactaacg aggtatataa    3180
attaaaaagt actagagtaa tactaatttt tatgtatgta ccatgtaatg tgaaataaat    3240 tcttctatttт atcaggtcaa gttattggta attatattgt ttatagtagg caattagcta    3300 gattaaaacta tataatataa aaaaatatat attagtaatc ttttgggat ttctcttttc    3360 ttagcctttc atatgtaatg gaacttgatg gcttgaaatg tagtttcatg tttttagaca    3420
gtcatctctg gtttcttcga aaagaaattc tgtgggtacc ccttctaatt cttaattagt    3480
tcactattga ttttacctct ataaattaaa tttgagtctg tatgtatatt tttgtttcaa    3540
actagtggtg tgcatcgacc taagttcgaa taaaaataga gttgctaaga t              3591
```

```
<210> SEQ ID NO 7
<211> LENGTH: 2756
<212> TYPE: DNA
<213> ORGANISM: Solanum lycopersicum
<220> FEATURE:
<221> NAME/KEY: mutation
<222> LOCATION: (1589)..(1589)
<223> OTHER INFORMATION: SNP14
<220> FEATURE:
<221> NAME/KEY: mutation
<222> LOCATION: (2146)..(2146)
<223> OTHER INFORMATION: SNP6
<220> FEATURE:
<221> NAME/KEY: mutation
<222> LOCATION: (2161)..(2161)
<223> OTHER INFORMATION: SNP2
<220> FEATURE:
<221> NAME/KEY: mutation
<222> LOCATION: (2313)..(2313)
<223> OTHER INFORMATION: SNP7

<400> SEQUENCE: 7
```

```
gcacattttt cacattatttт ctaagtttgt tgccatatga tataagggggg aaaaggtggt     60 aattacagat tcctcctcca tcattcattt gtaagttctc ctaaaagtcc tatctcatat    120
tatattatcc taaattttat ctttttcaat atatttatt ttcaggtaaa taagaatttt    180
attttcaaag aaaagtgtat cgttcaaaaa aaaatagaaa gaaattattc tgactagatc    240
aaatattagt taatttcatt ttgagacagc ctttgaaata tagatattaa attattctct    300
tcattaacat atcgatactt tgttgaaaaa caattttatt cctctcttat catatatgat    360
aatgcagccg gttaaggata tattgttgtt atagcactat cttgctcaga actgtgtata    420
ccaagtcaaa taattttcaa atgtacatgt ctctttttta aaagttaaat atatttgcac    480
ctactttttg cacaaataaa tgtgtgcaca ttagtttggc gaccatgtgt gatgtgtcgt    540
gcctgtgggg ttcatagttt ggcgcagtag tttgtcgcag ccaaagacag tttaaggaa    600 caacttcata tatagcaaat aaaaaatata tatttgtatg ttataacaaa atttgtataa    660
```

```
ttgcgttaca taataaacat ataactgtat aattcgctgg cctaaattgt ataattcgct    720
gacctatttc gctgcaattg tataattcgc tcgcctattt cactgcagtt gtataatgcg    780
caattatata attcgctgac ctattttgct ggaatatgtg tataaaattt gctttgcata    840
caattaaatc gaagtaaaag gtttatatat tgtataatta aagtgtata tataggaaga    900 agatatatgt ttttcgcttg ctttatacaa aaacagaaac acaatttata cacttctgtt    960
gtataaagcg agataattcg ttggcgtttt tcgctgtaat atttgtataa aatttgcatt   1020
tgtatacaat tgaatcgaag taaaatattt ttaaattgta taattaagtg tatagcacga   1080
aaatatacat tttttacatg tgtatataca attttctctc gctttataca aaacaaaaat   1140
acaatttata cacttctgtt gcataaagcg agagaggcaa gcagatggag agtggtgagc   1200
gagagttttg gaagagaggc gactggcaaa gacaaaggtt tgctatgaag cacaattaaa   1260
tcaaacagta actactccat ttattttagg ttactaattt gctactatat agaattatcc   1320
cttaataaaa ttcttatcat atagtataat atatgaattg aatacccatc atttcaaaaa   1380
attaaactag tcatttgaat gtctatatca ttataaaacc atgtgaaaaa ttagattatt   1440
cttcgtgtaa attactcgct cagtcttatt tatctttta gtctgattca cataatttt    1500 aaaagtttta cataacatgt ttaaaatcat aaaattaaag acattaatat atatttacac   1560
atctttaatt tatgacatat attttttttt aaaaaatctt ttttaaatta attttaaatt   1620
aaaataataa aatgaaacac ataaataaag taataataat tatcatcgta tattgatgaa   1680
caaatgagtt gatgtttgat cctattctta gtcaagcaaa tagaagtcta aattagcact   1740
ttttgttttt aatttattga tgattcatga accttgtttg ttaaattcaa gactatatat   1800
tacagtcaat tgtaaaacaa aatgtcttgg aaaattagat cctttattg gcccaccaaa   1860 tagacctagg aaacccatac gaacccagtg aagtcacatc gatgtggagt ctctagaacg   1920
tcaaatgtga gtcatcttgc tcatcctttt gtcgaaattt cttctattgg gtcaaataag   1980
aaatatgtgc cattctcgtt cttattaaat agacataata tacacttta attaaattaa   2040 tatgtgtcat gtaatgattt gtacgtaaat atgactgatt taaaataat ataataataa   2100 ttgttcaaaa ttacatagtg aattaataga taattacaaa ataagttgtc ttttaaaaa   2160 tcttggacaa cttcaatggt gtctttactt cgttttctct ttataaattt aaagcaaaaa   2220
aatatttata tgatgtcaat tgaccaaaca catggatgac ctggatctaa tttcttcgaa   2280
gagcattatc tcatcttgtt tatttggagt actatctttt cttatctcac tgaatgccta   2340
caaactaagc ataattttat tcttctgaag attagcttgc tcataaaacc ctcgtatcat   2400
tttgagctat ttgtaattga aaacgatgtt ttcatcacta ttatttattt taaaaggcg   2460 ttttttttcga gcaataaatt ctctttattt taatggtggt caattatgt tcaatttct    2520 tatcgtacat aacaattaac taaactttga aatatcaacg caaacaaggg gtaattaatt   2580
aaaccatgtc acaacccatc aagacaccaa ctatataata taaattgaaa aagacgtgca   2640 caattttttca cttgtttcct tatactttcc ttttctccaa cgagataaat aaaattcata   2700
aaaagagccc cacgattaaa cgattacttt tctagtattc ctttatgtta aatacc       2756
```